United States Patent [19]
Goumeniouk et al.

[11] Patent Number: 6,046,019
[45] Date of Patent: Apr. 4, 2000

[54] DIAGNOSTIC KITS AND METHODS FOR MAKING GRANULOCYTE CELL COUNTS

[76] Inventors: Alexander P. Goumeniouk, P.O. Box 91427, West Vancouver, British Columbia, Canada, V7V 3P1; B. G. Richards, 2342 Queens Avenue, West Vancouver, British Columbia, Canada, V7V 2Y6

[21] Appl. No.: 07/896,209

[22] Filed: Jun. 10, 1992

Related U.S. Application Data

[63] Continuation-in-part of application No. 07/727,582, Jul. 9, 1991, abandoned.

[51] Int. Cl.[7] .............................. C12Q 1/28; C12Q 1/00; G01N 33/53
[52] U.S. Cl. .............................. 435/28; 435/7.24; 435/4; 435/2; 436/18; 436/17
[58] Field of Search .................................. 436/6, 17, 18, 436/63, 66, 166, 71, 904; 435/4, 14, 11, 28, 7.24, 2

[56] References Cited

U.S. PATENT DOCUMENTS

| | | | |
|---|---|---|---|
| 2,799,660 | 7/1957 | Nicholls et al. | 252/408 |
| 2,848,308 | 8/1958 | Free | 23/253 |
| 2,905,594 | 9/1959 | Morris | 125/103.5 |
| 3,087,794 | 4/1963 | Free et al. | 435/11 |
| 3,552,928 | 1/1971 | Fetter | 435/11 |
| 3,741,875 | 6/1973 | Ansley et al. | 195/103.5 |
| 4,299,917 | 11/1981 | Berger et al. | 435/19 |
| 4,816,168 | 3/1989 | Carrol et al. | 210/782 |
| 4,826,872 | 5/1989 | Terao et al. | 514/474 |
| 4,844,818 | 7/1989 | Smith | 210/789 |
| 4,849,342 | 7/1989 | Ben-Michael | 435/7.9 |
| 4,957,638 | 9/1990 | Smith | 210/782 |
| 5,128,265 | 7/1992 | Meiattini | 436/17 |

FOREIGN PATENT DOCUMENTS

| | | |
|---|---|---|
| 1180-001 | 9/1985 | European Pat. Off. . |
| 418486 | 3/1991 | European Pat. Off. . |
| 418486 A2 | 3/1991 | European Pat. Off. . |

OTHER PUBLICATIONS

Griswold et al., Method for Quantification of Myocardial Infarction and Inflammatory Cell Infiltration in Rat Cardiac Tissue, Journal of Pharmacological Methods 20, 1988, pp. 225–235.

Mullane et al., Myeloperoxidase Activity as a Quantitative Assessment of Neutrophil Infiltration into Ischemic Myocardium, Journal of Pharmacological Methods 14, 1985, pp. 157–168.

Venge et al., Neutrophil and Eosinophil Granulocytes in Bacterial Infection: Sequential Studies of Cellular and Serum Levels of Granule Proteins, British Journal of Haematology 38, 1978, pp. 475–483.

Zubay, Biochemistry, The Benjamin/Cummings Publishing Company, Inc., Menlo Park, California, 1983, p. 234.

Procedure No. 380, Sigma Diagnostics, Clinical Technical Service, St. Louis, Missouri.

*Primary Examiner*—Louise N. Leary
*Attorney, Agent, or Firm*—Richard D. Multer

[57] ABSTRACT

Methods for detecting granulocytes and for providing an at least semiquantitative indication of granulocyte level and kits for implementing those methods. A blood sample is drawn, and components that might interfere with the assay are removed and/or neutralized. Granulocytes present in the sample are then disrupted to release intracellular myeloperoxidase, and the sample is contacted with a peroxide and a chromogenic donor dye. The myeloperoxidase enzyme catalyzes hydrogen peroxide-involved reactions which result in the dye changing color if, and to the extent that, granulocytes are present in the blood sample.

25 Claims, 11 Drawing Sheets

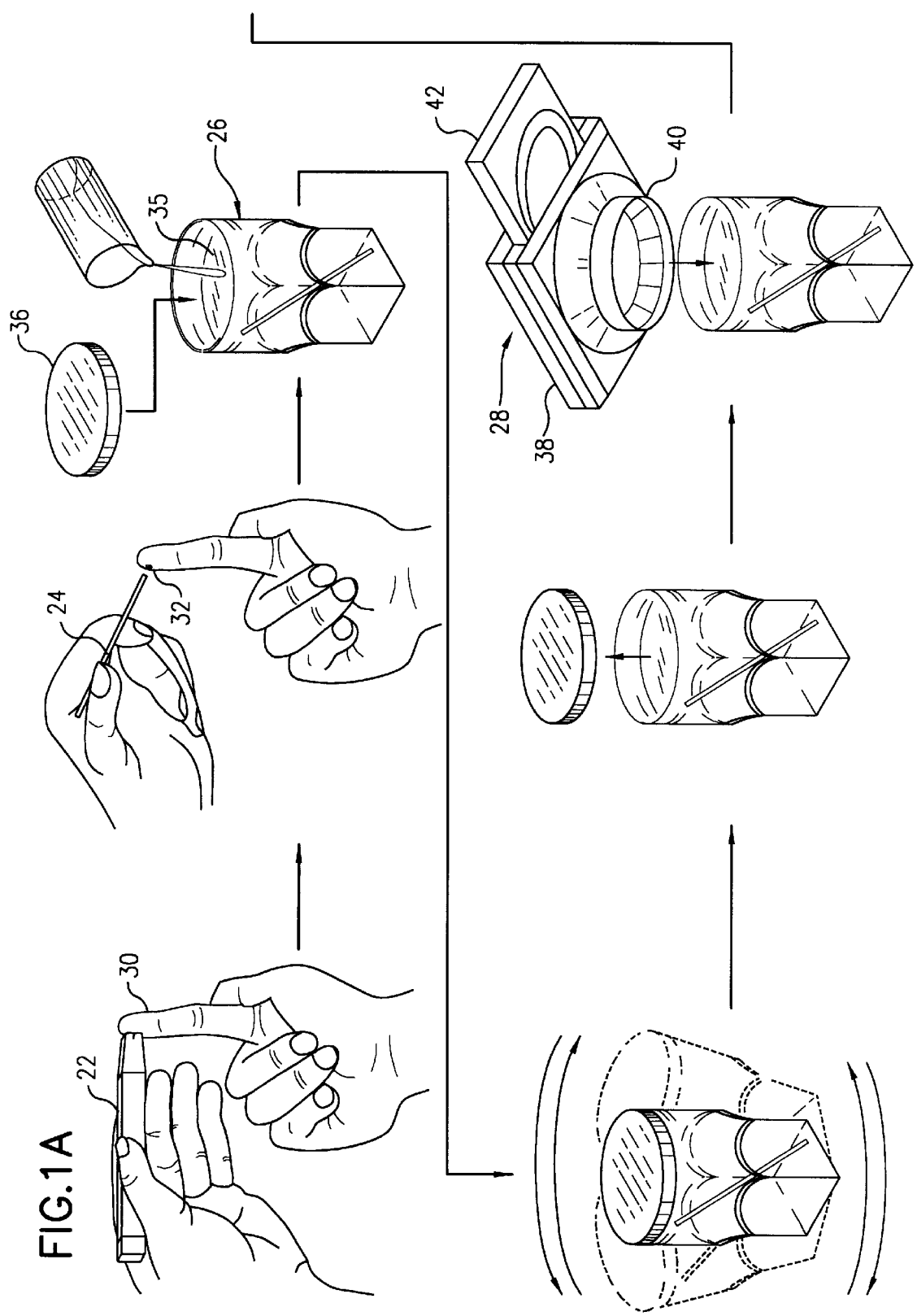

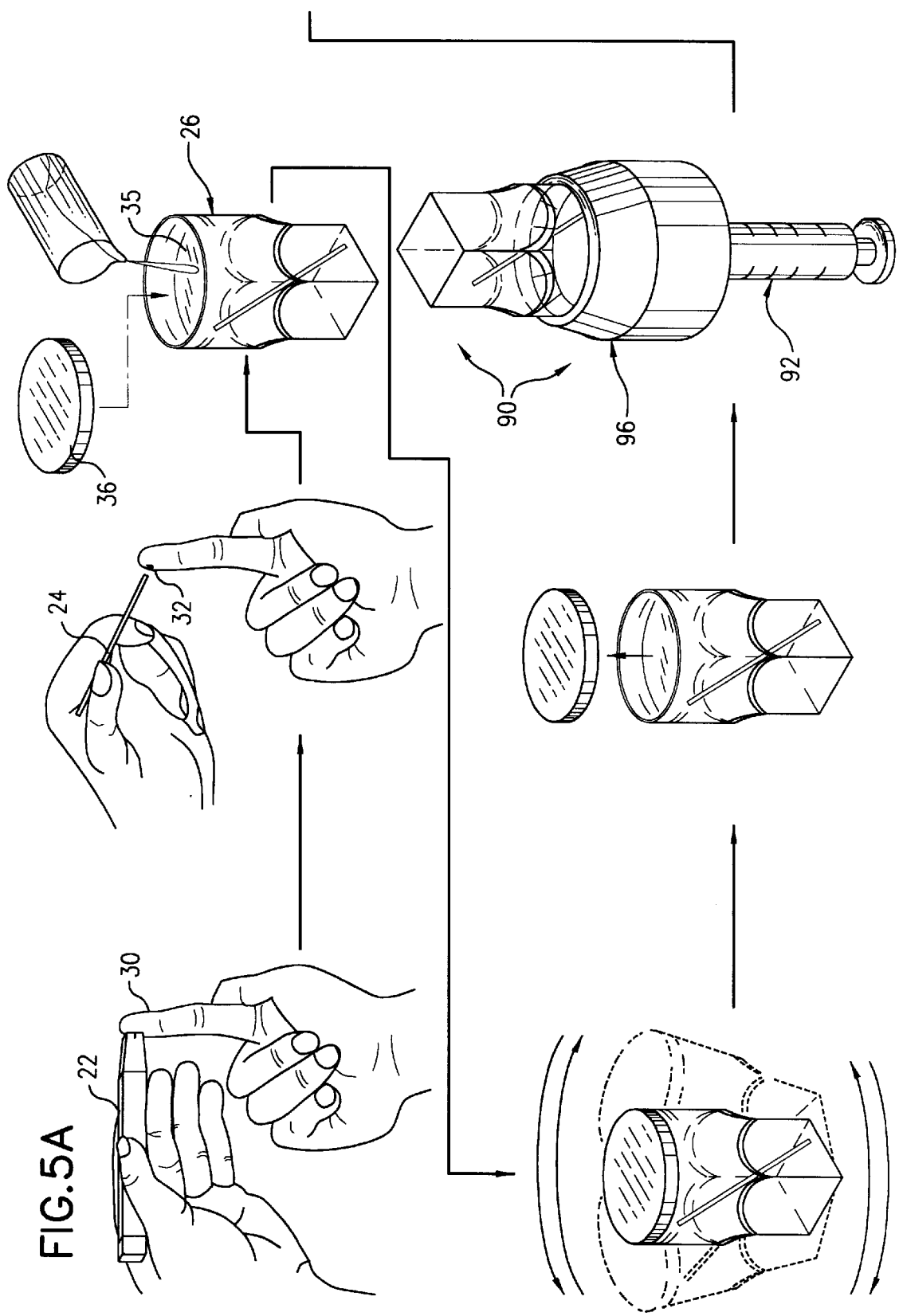

DIAGNOSTIC KITS AND METHODS FOR MAKING GRANULOCYTE CELL COUNTS

RELATION TO OTHER APPLICATION

This application is a continuation-in-part of application Ser. No. 07/727,582 filed Jul. 9, 1991, now abandoned.

FIELD OF THE INVENTION

The present invention relates: (a) to novel, improved methods for determining whether granulocytes are present in a blood sample and for making a granulocyte cell count, and (b) to novel kits for making those determinations and analyses.

BACKGROUND OF THE INVENTION

Blood serves as a chemical transport and communication system for the body. It contains a number of structurally and functionally diverse cellular components. The major components are red cells, platelets and white blood cells, or leukocytes. These components are sub-divided, and granulocytes comprise the major fraction of the leukocytes. Granulocytes are a vital component, providing body defenses against infection. One of the characteristic responses of the body to infection is an elevation in white blood cell count. Although infections are usually associated with an increased white cell count, decreases can also occur, especially if the bacterial invasion is massive or if the causative agent is a virus. Such decreases are usually due to a generalized depression of the bone marrow.

A rare, but potentially life-threatening complication of several drugs with otherwise beneficial therapeutic properties is their ability to inhibit granulocyte production by the bone marrow. In most cases, the development of the toxic side effect is unpredictable and does not become manifest until severe clinical complications are apparent. Thus, early recognition of an impairment in granulocyte formation, signalling the need for appropriate preventive measures, would greatly reduce the risk associated with the use of drugs known to be capable of interfering with granulocyte formation.

Predominant in granulocyte populations are the neutrophils or polymorphonuclear leukocytes. The neutrophils engulf foreign particles, for example bacterial cells, by phagocytosis which is facilitated by prior coating of the target by proteins known as opsonins. This initial step is followed by decomposition of the engulfed species by intracellular processes involving the combined action of degradative enzymes and of chemically reactive products of oxygen.

An important component in the generation of the reactive products of oxygen is the enzyme myeloperoxidase (MPO) which has been used as a marker for neutrophils. The action of MPO on intracellular chloride ions in the presence of metabolically generated hydrogen peroxide produces hypochlorous acid, which chemically degrades the foreign particles.

Important leukocyte disorders primarily involve changes in either the functional characteristics of the leukocyte or in the number of circulating leukocytes. One example of the former is chronic granulomatous disease in which granulocytes show a reduced capacity to generate reactive oxidant species in the so-called "respiratory burst" which normally destroys microorganisms that have been engulfed by phagocytic cells. Individuals affected with granulomatous disease usually die at an early age because of an inability to combat infection.

Granulocytes may increase in number in certain instances, usually in association with infection or a leukemic condition. Conversely, the clinical situation in which granulocyte numbers are reduced relative to normal also occurs. This condition, granulocytopenia, is the most frequent cause of drug or disease related alterations in body defenses against infection. Agranulocytosis, an extreme form of this disorder, is characterized by a severe and selective drop in the number of circulating neutrophils, predisposing the patient to serious and possibly even life-threatening infections. Any form of granulocyte deficiency has potentially serious clinical consequences, and early identification is crucial if the consequences of those deficiencies are to be averted.

A white blood cell count is one of the most commonly obtained laboratory values in clinical medicine. Total cell counts can be obtained by using automatic electronic devices available in clinical analytical laboratories. The quantitative assessment of individual blood cell types (the "differential count") is made by manual microscopic examination of stained blood smears or with an automated system such as a Coulter counter. Nevertheless, a white blood cell test requires a visit to a physician, a 7 milliliter venous blood sample and up to a three-day wait for laboratory results. In addition to inconvenience, delayed test results can severely affect the prognosis of a patient.

These drawbacks are compounded by virtue of white blood cell counts being probably the most commonly obtained laboratory values in clinical medicine. The cost of obtaining white blood cell counts is staggering, even not taking into account the cost of the time lost by those for whom this test is ordered.

The relative proportions of the different white blood cell types is of considerable importance in assessing the clinical implications of any leukocyte deficiency state (leukopenia). Thus, for example, a marked reduction in leukocyte levels can sometimes be fairly well tolerated provided that neutrophils comprise at least 15 to 20 percent of the total white cell population, compared with the normal range of 40 to 70 percent.

Neutrophil status is a very important diagnostic indicator, not only because of the crucial role of these cells in the defense against infection, but also because the average lifetime of neutrophils in the body is very much shorter than that of other types of blood cells such as red cells or platelets. As a result, decreased levels of circulating neutrophils can provide an early warning of impairment in bone marrow function which can occur in association with certain disease states or as a serious, and potentially fatal, complication of drug therapy or exposure to radiation. A state of neutrophil deficiency (neutropenia) is generally assumed to exist if the number of cells falls below 1,500 cells per microliter of blood. However, a considerable range of "normal" values exist for numbers of circulating leukocytes. Many blacks and Middle Eastern populations have neutrophil counts considerably lower than those of the average European.

In some cases, neutropenia can be anticipated and appropriate measures taken to minimize the risks. For example, patients receiving chemotherapy for the treatment of acute leukemia are prone to develop neutropenic enterocolitis which is caused by bacterial overgrowth in the intestinal tract. Although often limiting, this condition can damage the wall of the intestine and even result in perforation of the bowel.

In contrast to the above, predictable, dose-related risk of neutropenia for anticancer drugs (which reflects the preferential action of the drugs on rapidly multiplying cells), the development of agranulocytosis is virtually unpredictable. Agranulocytosis is a rare but potentially fatal toxic side effect of several commonly used therapeutic agents. The incidence seems to increase substantially over age 40 with an apparent increased risk in females.

Two different forms of the syndrome can be distinguished. The allergic type usually appears suddenly after the initial exposure to the drug, while the toxic variety develops insidiously over several weeks or months of continuous or intermittent therapy. Among the pharmacological agents most commonly implicated are certain antibiotics, notably the sulphonamides and chloramphenicol, antithyroid drugs (thiouracil and propylthiouracil), gold compounds, non-steroidal anti-inflammatory drugs and some antipsychotic agents, for example, chlorpromazine and clozapine.

The mechanism underlying this apparent drug sensitization is unknown. The issue of blood monitoring while a patient is being treated with an agent known to be capable of inducing agranulocytosis is clearly an important one to consider, and two salient points should be made. The first is that the onset of agranulocytosis need not be associated with the immediate development of a full-blown infection although, in the absence of routine monitoring of leukocyte status, signs of infection, notably fever or sore throat, are likely to be the first indication of the problem. As a general rule, antimicrobial therapy initiated after an infection has progressed to the symptomatic stage is likely to be less effective and to require more aggressive measures than preventative interventions. This is particularly so in the case of patients with deficient neutrophil or immune status. Secondly, continued use of an agranulocytosis-producing drug in the early, symptom-free phase of the disease can lead to a serious deterioration in the condition of the patient. Both of these conditions, therefore, require frequent assessment of leukocyte status in patients receiving drugs known to produce agranulocytosis.

There are two deterrents to this otherwise sensible, frequent monitoring of white blood cell count—cost and inconvenience. There is not currently available an inexpensive monitoring device or procedure which provides for the early detection of a significant decrease in granulocyte count that could warn of the onset of conditions such as agranulocytosis with a resultant increase in the acceptability and safety of therapeutic regimens employing drugs tending to produce this and other health and life threatening decreases in granulocyte count.

Increased circulating levels of neutrophils—for example, counts in excess of 10,000 cells per microliter of blood—are a common manifestation of infection. Microbes release chemotactic substances which can increase neutrophil activity. This involves both a stimulatory action at the level of the bone marrow and a mobilization from a less accessible marginal pool of neutrophils which are largely confined to the immediate vicinity of blood vessel walls. These partially sequestered leukocytes respond to chemical signals released from microorganisms or damaged tissues and accumulate rapidly at the site of microbial attack or injury. A typical example of the latter is the infiltration of neutrophils which is a characteristic feature of the inflammatory response.

The stimulatory action of microbial toxins on bone marrow can lead to large elevations (up to tenfold) in the number of circulating neutrophils. In some instances, such marked responses may be accompanied by the appearance of immature neutrophil precursor cells. This is referred to as the leukemoid reaction because of the similarity to a situation that exists in leukemia.

Myeloperoxidase (MPO) has been employed as a marker for granulocytes in a variety of clinical and experimental settings. This enzyme is an iron containing protein that catalyzes a reaction between hydrogen peroxide and chloride ion which produces hypochlorous acid. This reaction is important in the characteristic respiratory burst that serves to destroy bacteria following their phagocytosis by granulocytes. The absence of detectable MPO activity in other cellular elements of the blood provides a way of quantifying the severity of tissue inflammation, which is reflected in the extent of granulocyte infiltration.

Measurement of MPO activity in whole blood has also been used in the diagnosis of patients with acute leukemia and to monitor bone marrow regeneration in such patients following treatment with drugs or radiation.

Estimates of MPO activity also form the basis of automated analysis of blood smears.

The activity of MPO can readily be determined using oxidation-sensitive dyes which undergo a measurable color change during the course of a chemical reaction. The nature of the color change depends on the chemical characteristics of the particular dye that is used.

One procedure of the character just described is disclosed in Russian document No. SU 1180-001-A dated Jul. 1, 1983 (IRKUT MEDICAL INSTITUTE).

Another procedure for making a white blood cell count, also designed for laboratory settings, is disclosed in U.S. Pat. No. 3,741,875 issued Jun. 26, 1973 to Ansley et al. for PROCESS AND APPARATUS FOR OBTAINING A DIFFERENTIAL WHITE BLOOD CELL COUNT. In the Ansley et al. process, blood cells in the specimen being analyzed are killed; and the catalytic enzymes in the cells are immobilized. The cells are stained, and a photometric counter is employed to count the dyed cells.

Like others designed for laboratory settings, those procedures disclosed in the just-cited documents employ steps requiring trained personnel and specialized equipment and materials such as incubators, optical counters, zytochemical substitutes, chromogenic precipitating coupling reagents, etc.

In an outgrowth of work on the detection and estimation of glucose (see U.S. Pat. No. 2,848,308 issued Aug. 19, 1958 for COMPOSITION OF MATTER), Free et al. proposed a test for detecting leukocytes by peroxidative activity. In this test, disclosed in U.S. Pat. No. 3,087,794 issued Apr. 30, 1963 for CHEMICAL TEST FOR DIFFERENTIATING LEUKOCYTES FROM ERYTHROCYTES, contact is effected between urine which may contain both leukocytes and erythrocytes and a diagnostic composition which contains a peroxide and an indicator compound. If the sample contains leukocytes, the peroxidative enzyme will be present; and the following reactions will occur:

peroxidase (enzyme)+$H_2O_2$ (substrate)→intermediate compound intermediate compound+$AH_2$ (hydrogen donor which will change color upon oxidation, reduced colorless form)→peroxidase+$H_2O$+A (oxidized, colored form)

A semiquantitative result can be obtained by measuring the time required for the color change to occur or by observing the change in intensity over a specified period of time.

The Free et al. process as applied to leukocyte analysis has very important drawbacks. One is that the test can't be applied to blood because of hemoglobin interference. Erythrocytes and leukocytes (red cells and white cells) both show peroxidative activity. The major difference is that leukocyte peroxidase is active at low concentrations of $H_2O_2$, while the peroxidative activity of erythrocytes is due to the peroxidase-like activity of the hemoglobin, which requires a much higher concentration of $H_2O_2$ to become operative. Therefore, the color reaction at a low concentration of $H_2O_2$ is due to the presence of leukocytes and the color reaction at a high concentration of $H_2O_2$ is due to the presence of red cells (especially since myeloperoxidase tends to be inhibited by high concentrations of $H_2O_2$).

A second major drawback of the Free et al. procedure is that no provision is made for releasing material with oxidative reactivity from the cells potentially present in the specimen before the determination of leukocyte activity is made. This deficiency is significant because the material in question is typically present inside the cell instead of on the cell surface, the marker enzyme myeloperoxidase for granulocytes being typical in this respect. Absent anything for releasing such materials, therefore, a false white blood cell count will almost certainly be obtained.

Another significant drawback of the Free et al. process as applied to the making of white blood cell counts is that no provision is made for eliminating interference from other blood components. Perhaps the most abundant source of this contamination is the enzyme catalase found in erythrocytes (red blood cells). Catalase can promote the same peroxide decomposition reactions as white blood cell markers such as myeloperoxidase. Consequently, absent a step to keep this from happening, a change in the color of an oxidation sensitive indicator as used by Free et al. may not reflect with any degree of accuracy the activity of leukocyte in a specimen being analyzed.

In short there is a continuing, important and unfilled need for a simple, inexpensive, easy-to-use, reliable procedure for making white blood cell counts and for a diagnostic kit implementing such a procedure which does not require skilled personnel or special facilities or equipment and can be used in home and other nonclinical settings with a minimum of instruction. This would, as one example, materially facilitate the treatment of infections as the efficacy of a selected course of treatment as a reflection of a change in granulocyte count could be much more easily ascertained. A procedure of the character in question would also significantly increase the ability to track the effect of those pharmacological agents which have the potential of producing a harmful change in white blood cell count.

There is a comparable need for methods and kits as characterized in the preceding paragraph which are sufficiently accurate and efficacious to be useful in diagnostic and monitoring protocols by more highly trained personnel in field, clinical and other settings.

SUMMARY OF THE INVENTION

Such procedures and kits for making white blood cell—specifically granulocyte—counts have blood cell—specifically granulocyte—counts have now been invented and are disclosed herein.

The procedures and kits of the present invention employ the action of MPO liberated from granulocytes on hydrogen peroxide to decompose the hydrogen peroxide and produce a visible color change in an oxidation-sensitive dye. The reaction can be quantified either in terms of the intensity of the color produced or the time required to achieve a given level or type of color formation. Deviations from a predetermined range of normal values denote a deficiency or an excess of granulocytes and provide an approximate indication of the severity and hence the urgency of the clinical situation.

The kit employed to carry out the foregoing steps includes: an instrument for taking a blood sample; an instrumentality for separating white blood cells from blood components that would obscure or introduce an error into a color change indicative of granulocyte count; an oxidation-sensitive indicator, typically a chromogenic donor dye; a peroxide; something to disrupt the leukocytes and effect a release of their intracellular myeloperoxidase (MPO); and an instrumentality inhibiting the activity of trace contaminants from red blood cells. These components are so designed that the kit can be employed with only a minimum of instruction and in home and other nonmedical settings as well as those field, clinical and comparable scenes in which more highly trained personnel may be available. At the same time, the components of the kit are selected for simplicity and cost effectiveness and so that reliable results can be obtained easily and rapidly.

Another advantage of the procedure and kit disclosed herein is that the specimen can be very small—for example, a blood sample obtained by a simple finger prick.

The potential savings to the health care system are enormous.

The potential beneficiaries of the present invention include but are not limited to:

patients with suppressed immune systems or with fevers and related symptoms;

acute situations in emergency rooms or at home; and users of prescription drugs which are known to induce abnormal white blood cell levels (antibiotics, anti-inflammatories, antithyroids and antipsychotics).

The objects, features and advantages of the present invention will be apparent to the reader from the foregoing and the appended claims and as the ensuing detailed description and discussion of the invention proceeds in conjunction with the accompanying drawing.

DETAILED DESCRIPTION OF THE INVENTION

Figure 1:
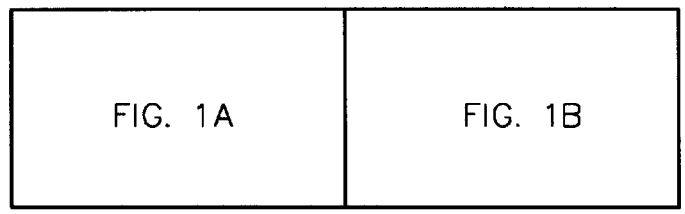
FIG. 1 illustrates the relationship of FIGS. 1A and 1B which, taken together, show one diagnostic kit embodying the principles of the present invention; that figure also shows how the kit is used to detect granulocytes and to make an at least semiquantitative evaluation of the granulocyte level.
Figure 2:
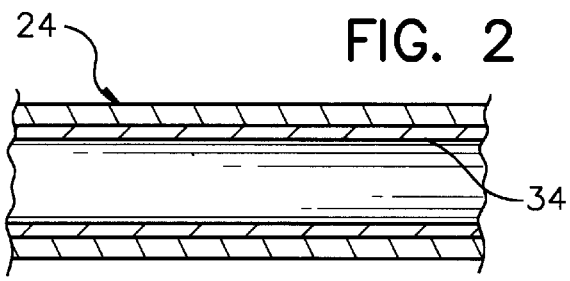
FIG. 2 is a fragmentary section through a microcapillary tube which is a component of the diagnostic kit illustrated in FIG. 1.

As discussed briefly above, the novel method of evaluating granulocyte levels disclosed herein takes advantage of the fact that myeloperoxidase promotes oxidation-reduction reactions between peroxides and oxygen sensitive dyes. The rate and extent of the color change in the dye reflects the concentration of this enzyme. Intracellular myeloperoxidase is found in granulocytes in amounts which are generally constant from cell-to-cell, and the rate and intensity of color change can accordingly be employed to accurately reflect the level of granulocytes in a blood sample being assayed. However, because myeloperoxidase appears as an intercellular component of a granulocyte, those granulocytes present in the sample being assayed must be lysed or disrupted to release the enzyme before the sample is treated with the peroxide and the dye to make a meaningful determination of granulocyte level.

Also, because both plasma and red cells contain peroxidase enzymes and because hemoglobin in red cells also has peroxidase-like activity under certain conditions, it is necessary to separate the white cells as completely as possible from the other blood components before the lysing and subsequent assay of the white blood cells is effected. White cells are more resistant to hypotonic lysis than red cells. Double distilled water and commercially available bottled water can accordingly be used to disrupt the red blood cells and release potentially interfering blood components which are removed from the white blood cells with the hypotonic lysing reagent by filtration.

Other lytic agents such as ammonium chloride, saponin and acetic acid/tartaric acid mixtures are also potentially usable to effect the release of potentially interfering blood components just described.

The filter employed to separate the thus released blood components which might interfere with an accurate determination of granulocyte presence and concentration is extremely important. It must be sufficiently absorbent to permit blood to be transferred directly onto it from a microcapillary tube (unless a prelysing step as described above is used). But, if the filter is too absorbent, once the blood is transferred and the lysing agent is added, a reasonable degree of agitation will not disperse the cells into solution so that the red cells will lyse well and the white cells will be evenly distributed over the entire filter after filtration. Also, it is preferred that the filter not absorb free hemoglobin because of the difficulty of quantifying color development with a high background red color and because of the peroxidase-like activity of hemoglobin. The pore size must be sufficiently small to retain the white cells (10–12 microns in size) but large enough to permit the hypotonic lysing solution and its burden of released blood components to flow through the filter at a reasonable rate.

The application of positive or negative pressure or a combination of positive and negative pressure to the prelysed blood sample can be employed to make the removal of the potentially interfering components more effective.

Once the white blood cells have been separated by the just-described prelysing step, an aqueous peroxide- and dye-containing indicator reagent or assay medium is added to the material remaining on the filter to provide the wanted indication of whether granulocytes are present in the blood sample being analyzed and the granulocyte level. Also, this reagent includes a detergent for lysing any present granulocytes to release the intracellular enzyme myeloperoxidase employed to catalyze color developing reactions between the peroxide and the dye.

Effective for this purpose are the polyethylene ether detergents marketed under the trademark Triton and hexadecyltrimethylammonium bromide. These detergents are typically employed in a concentrations of ca. 0.005%.

The preferred peroxide is hydrogen peroxide. However, urea hydrogen peroxide or cumene hydroperoxide may also be employed as can an in vitro hydrogen peroxide generating system composed of glucose oxidase and glucose constituents which are combined immediately before the indicator reagent is used.

Hydrogen peroxide concentrations of 0.0005 to 0.00065 percent (30 percent stock solution) are preferably employed, and the concentration is important. Color may not develop if lower concentrations are used. If the concentration is too high, the peroxide may be catalyzed by hemoglobin that happens to be present, producing a blue color that is not related to the presence of granulocytes.

The assay medium will typically have a pale red-brown tinge after the blood sample is added. This may rule out, as a practical matter, the use of otherwise suitable oxidation sensitive, chromogenic donor dyes because those dyes go from colorless to red in the myeloperoxidase-promoted reactions discussed above; and this color change is obscured by the color which the blood sample imparts to the reagent. Consequently, the preferred dye is o-tolidine, which goes from colorless to blue under the same conditions. o-tolidine is preferably employed in a concentration of 0.08 to 2.0 milligrams per milliliter of the reagent in which the dye is incorporated. Higher concentrations may result in the dye precipitating out and becoming ineffective or in the dye interfering with the myeloperoxidase-catalyzed reactions. Concentrations below the stated level may result in an undetectable color change, especially if the granulocyte concentration in a sample is low, and in the developed color becoming unstable over time.

Other candidates for the chromogenic donor dye are 3,3',5,5'-tetramethylbenzidine and 2,2'-azinobis(3-ethylbenzthiazoline-6-sulfonic acid).

Prelysing of a blood sample in a hypotonic solution to disrupt red blood cells present in the blood sample being analyzed and thereby liberate components of those cells which might interfere with the assay can result in potentially interfering blood components being left with the white blood cells after the subsequent filtration step. One of these components is catalase. Like myeloperoxidase, this enzyme possesses the ability to decompose hydrogen peroxide. Consequently, unless this enzyme is neutralized, it may also effect a change in the color of the oxygen sensitive dye, thereby causing the assay to reflect a higher level of granulocytes then is actually present.

In the present invention, this neutralization can be effected by incorporating a catalase inhibitor in the aqueous based reagent. Preferred is 3-amino-1,2,4-triazole, which inhibits catalase but not myeloperoxidase. The triazole is preferably employed in a 30–75 millimole concentration. That concentration is high enough to neutralize the enzyme without causing solubility problems.

The interference problem discussed in the preceding paragraphs can also be eliminated by employing a filter with appropriate characteristics. For example, if the Whatman GF/C glass microfilter described hereinafter is employed, an inhibitor is required. In contrast, an inhibitor is not needed if a Micron Separations, Inc. Magna Nylon supported plain filter is used.

Hypotonic lysing or washing with an aqueous medium such as distilled water can also be employed to disrupt red blood cells present in the sample being analyzed for granulocyte concentration and to remove potentially interfering blood components such as hemoglobin from the sample. The application of positive or negative pressure or a combination of positive and negative pressure to the blood sample can be employed to make the removal of the potentially interfering components more effective.

To further promote test result accuracy, the reagent solution is preferably buffered against those pH changes that would otherwise occur as the dye containing reagent is added to the prelysed blood sample and as chemical reactions take place in the reagent. Citrate buffers with a pH in the range of 4.0 to 5.0 and phosphate buffers with a pH in the range 6.0 to 7.0 and preferably in the range of 6.0 to 6.5 can be employed with a pH in the range of 5.0 to 7.0 being employed when o-tolidine is the chromogenic donor dye. Buffers with higher pH's are avoided as the dye will then turn a light brown rather than the wanted distinctive blue.

Specific buffers that are satisfactory and have the requisite pHs are: (1) a mixture of sodium dibasic phosphate and potassium monobasic phosphate (phosphate buffer), and (2) a mixture of sodium citrate and citric acid (citrate buffer).

Typically, a 50 mM concentration of the selected buffer will be employed; but this is not critical. What is important is that the concentration not be too low—in which case the pH will fluctuate instead of remaining stable—or too high. In the latter case the buffer may precipitate other constituents of the reagent. At the appropriate pH, the development of color is completed within a few minutes; and there is sufficient difference in the color developed by blood samples with different granulocyte counts to allow one to estimate the granulocyte level in the sample with a reasonable degree of accuracy.

Another circumstance in which a buffer of specific pH can be employed to advantage is that in which the sample contains an elevated granulocyte count. In this case, the development of color in the oxidation sensitive dye to a maximum intensity may occur so quickly that the development of color cannot be timed in a fashion accurately reflecting the actual granulocyte count. For example, if it is the intensity reached after one minute that is being used as a reflection of granulocyte count, and maximum intensity is reached in 30 seconds, the test is less meaningful. In these and comparable cases, a less acidic buffer such as a citrate buffer with a pH of 5.0 is employed to slow down the color change reaction so that the color change will only be of an intensity reflecting the actual granulocyte count over the selected time measurement period. This allows the observer to clearly discriminate between samples with different granulocyte levels.

Figure 10:
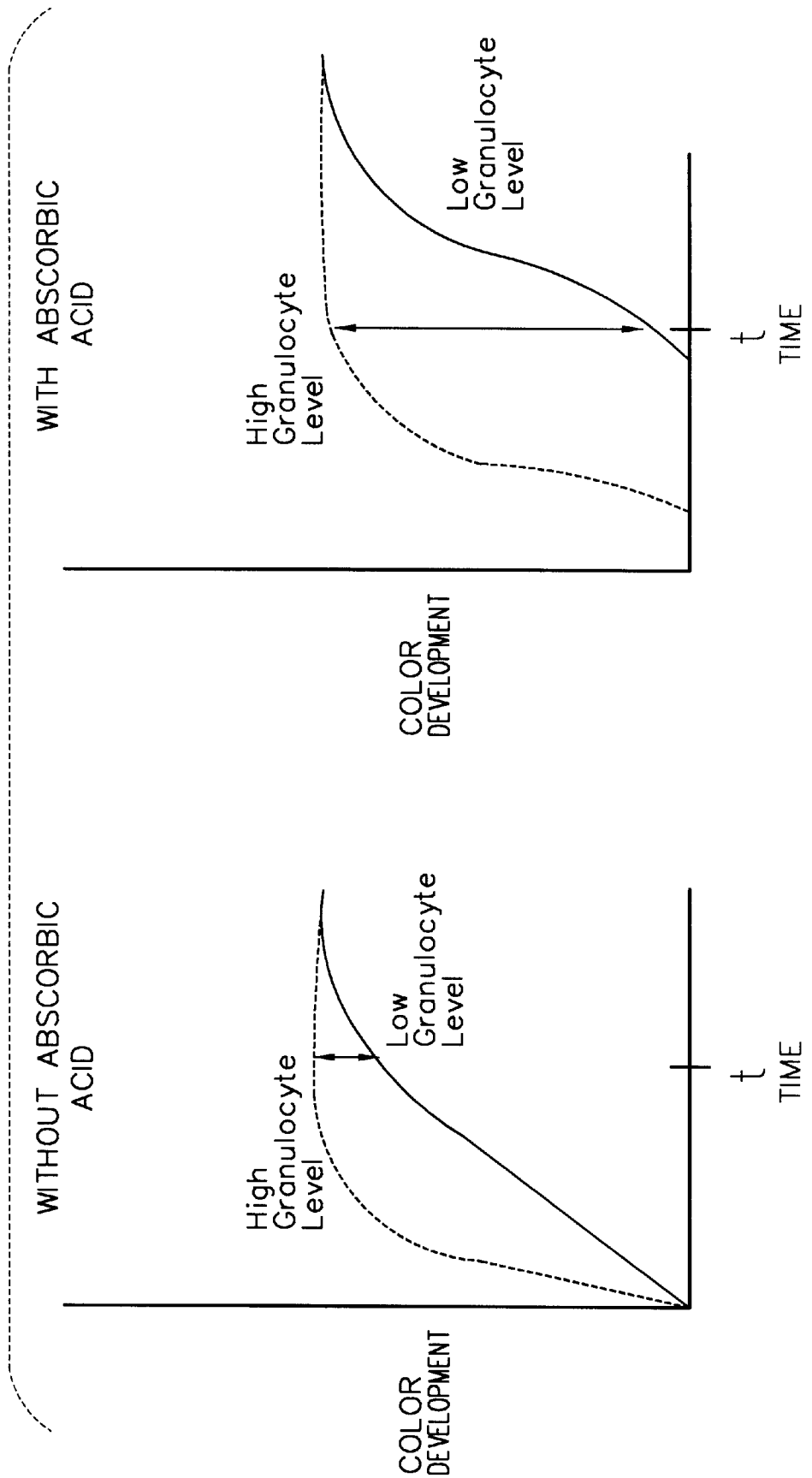
FIG. 10 contains a pair of graphs showing the effect of a proton donor on the development of color in an assay medium used in accord with the principles of the present invention to detect granulocytes and provide indications of granulocyte levels.

Optimal results can also often be obtained by altering that point in time at which a myeloperoxidase-promoted reaction of the peroxide in the assay medium will effect a change in the color of the oxidation sensitive dye. This can be controlled by adding a proton donor to the assay medium. One suitable donor of this character is ascorbic acid in a concentration of not more than one millimole. This is low enough to keep the acid from unduly delaying or even preventing a color change while keeping the color change from occurring too rapidly and impairing the resolution of the change (see FIG. 10 which shows that the ascorbic acid proton donor has the effect of making the difference in color development attributable to high and low granulocyte levels much greater at the representative time t after the indicator reagent is added to the residue from the filtration step).

Referring now to the drawing, FIG. 1 depicts a diagnostic kit which embodies the principles of the present invention and is designed to detect granulocytes and to provide an at least semiquantitative indication of granulocyte level. The major components of the diagnostic kit are a lance 22, a microcapillary tube 24, a cuvette 26 and a disposable assay device 28 with components typically molded from an appropriate thermoplastic polymer.

Lance 22 is employed to draw blood, typically from the subject's finger 30 as shown in FIG. 1A.

A quantitized sample 32 of the blood is taken up with the calibrated microcapillary tube 24. Microcapillary tube 24 has a silicon coating 34 which keeps the blood from coagulating. An alternative is to use a microcapillary tube or pipette to which an anticoagulant has been added. Anticoagulants that can be used include $K_3EDTA$ and sodium heparin. No obvious differences in the effectiveness of these anticoagulants have keen found except that, on occasion, some samples that were obtained with heparin as the anticoagulant (especially when the heparin concentration was somewhat high) tended to show a non-uniform color development in the test. This is consistent with the known clumping effect of heparin on white blood cells.

The microcapillary tube 24 with blood sample 32 is dropped into cuvette 26 which is a standard, commercially available item. A prelysing reagent 35 which is distilled or bottled water as described above is added, and the cuvette is closed with lid 36.

The next step in the procedure, also shown in FIG. 1A, is to vigorously shake the sealed cuvette 26. This generates mechanical forces which promote the disruption of the red blood cells in the sample, facilitating the separation of potentially interfering blood components from any granulocytes present in the sample.

At the end of the prelysing step, lid 36 is removed; and cuvette 26 is assembled to assay device 28.

Figure 1B:
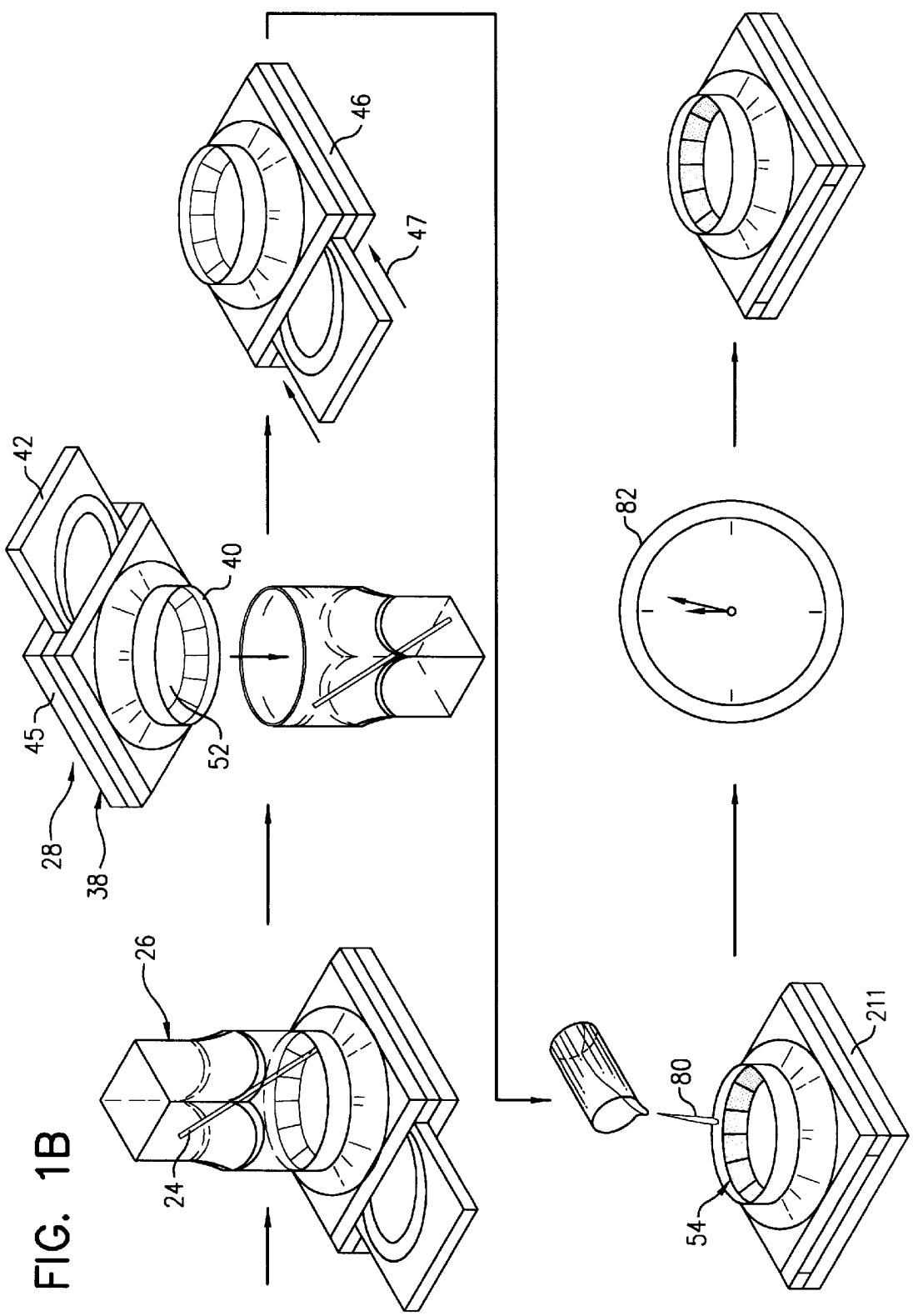
Figure 3:
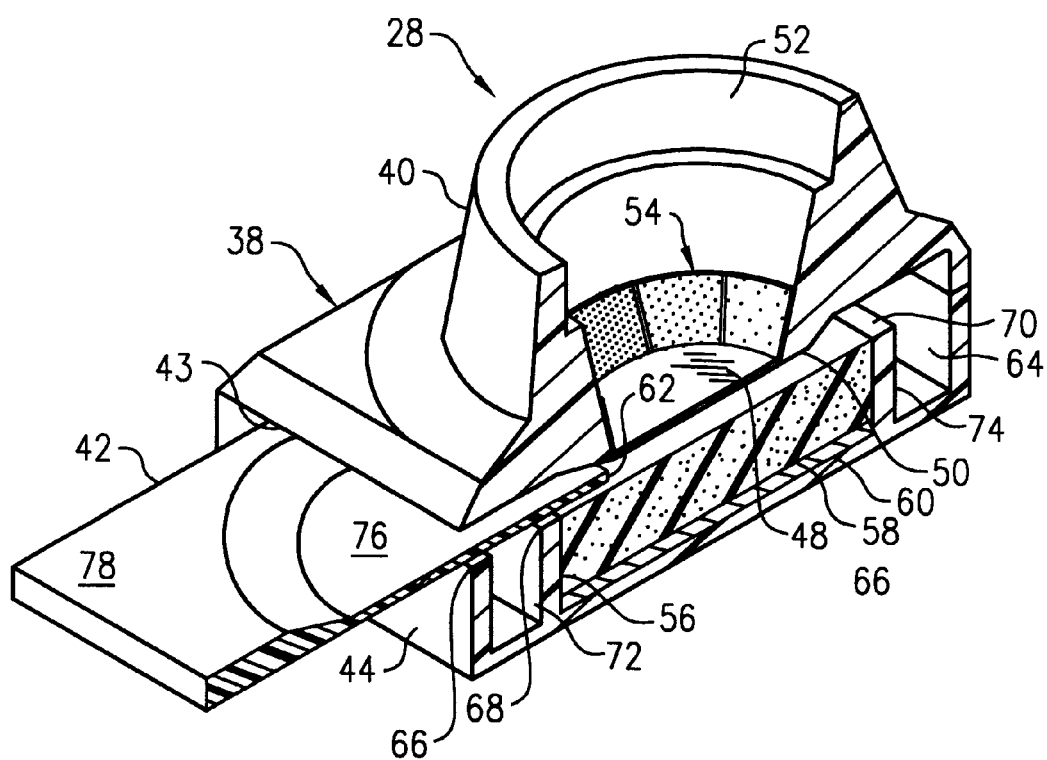
FIG. 3 is a partially sectioned isometric view of an assay device which is a component of the diagnostic kit.

As is shown in both FIG. 1A and FIG. 1B, and in more detail in FIG. 3, this device includes a base 38 with a hollow, cylindrical boss 40 and a slide 42 which extends through a slot 43 in base end wall 44. The slide is trapped between side walls 45 and 46 of base 38 and can be displaced from the illustrated "open position" in the direction indicated by arrow 47 in FIGS. 1B and 3 to a "closed" position also shown in FIG. 1B.

Assay device 28 also includes a porous membrane 48 spanning tie lower end 50 of the cavity 52 in boss 40 and a frustoconical color standard 54 in cavity 52 immediately above the porous membrane.

Membrane 48 is fabricated from a microporous material which has the ability to retain structural integrity when it is netted. Suitable is Whatman™ GB/C glass microfiber material.

Also part of assay device 28, and housed in a recess 56 in base 38, are a block 58 of absorbent material and, beneath that block, a thin layer 60 of a friable or crushable polymer.

As is shown in FIG. 1B, the assembly of cuvette 26 and assay device 28 is turned upside down to directly transfer its contents from cuvette 26 to assay device 28. With the slide 42 of the assay device in the open or out position shown in FIGS. 1B and 3, the lysed granulocytes are trapped on membrane 48 while the liquid phase of the cuvette contents passes through this membrane and is absorbed by the block 58 of absorbent material, which thus isolates the unlysed white blood cells from the filtrate composed of the prelysing reagent and potentially interfering blood constituents released to the reagent in the prelysing step.

Next, cuvette 26 is detached from assay device 28; the assay device is inverted; and slide 42 is closed—i.e., displaced into base direction indicated y arrow 47. Slide 42 moves rectilinearly into the base beneath membrane 48 until its inner end 62 reaches end wall 64 of the base. It is guided through this path by the bottom edge 66 of slot 43 and the upper edges 68 and 70 of the internal walls 72 and 74 defining the ends of the recess 56 in which assay device components 58 and 60 are housed.

It is important, in closing slide 42, that it not rupture the membrane 48 on which the lysed granulocytes are trapped. Tearing is prevented by the depression 76 in the upper side 78 of the slide and by the friable material 60 in the bottom of absorber recess 56. As the block 58 of absorbent material absorbs fluid passing through membrane 48 and expands, layer 58 collapses, keeping the swollen absorbent material from pressing against and tearing the membrane.

Referring again to FIG. 1B, the closing of slide 42 in the manner just described isolates membrane 48 and the lysed granulocytes trapped on that membrane from absorbent material 58. This keeps potentially interfering blood components from migrating back through the membrane to the trapped granulocytes.

Next, as is also shown in FIG. 1B, a selected quantity of the chemical reagent or assay medium 80 is poured onto membrane 48 to effect the release of intracellular myeloperoxidase from the granulocytes and thereby catalyze the color development reactions between the peroxide and the chromogenic donor dye in the assay medium. After a period of selected duration measured by timer 82, the then altered color of the chemical reagent is matched with one of the segments 84-1 . . . 84-7 of first zero and then increasing intensity on color standard 54. Each of these segments corresponds to a different granulocyte count beginning with zero (segment 84-1). Consequently, the matching step just described provides an at least semiquantitative indication of the granulocyte count in the sample of blood being analyzed.

Alternatively, the granulocyte count can be made by latching the color developed in the indicator solution with a particular segment 84 of color standard 54 and noting the time required for the color to develop.

Figure 5:
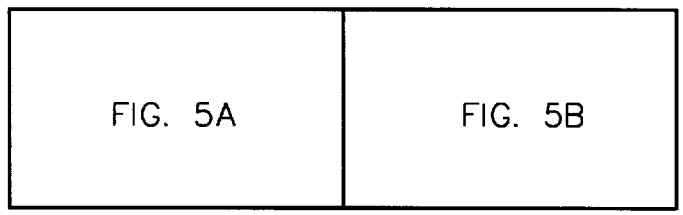
FIG. 5 shows the relationship between FIGS. 5A and 5B which, taken together, depict a second diagnostic kit embodying the principles of the present invention and shows how that kit is used to detect granulocytes and provide indications of granulocyte levels.
Figure 5B:
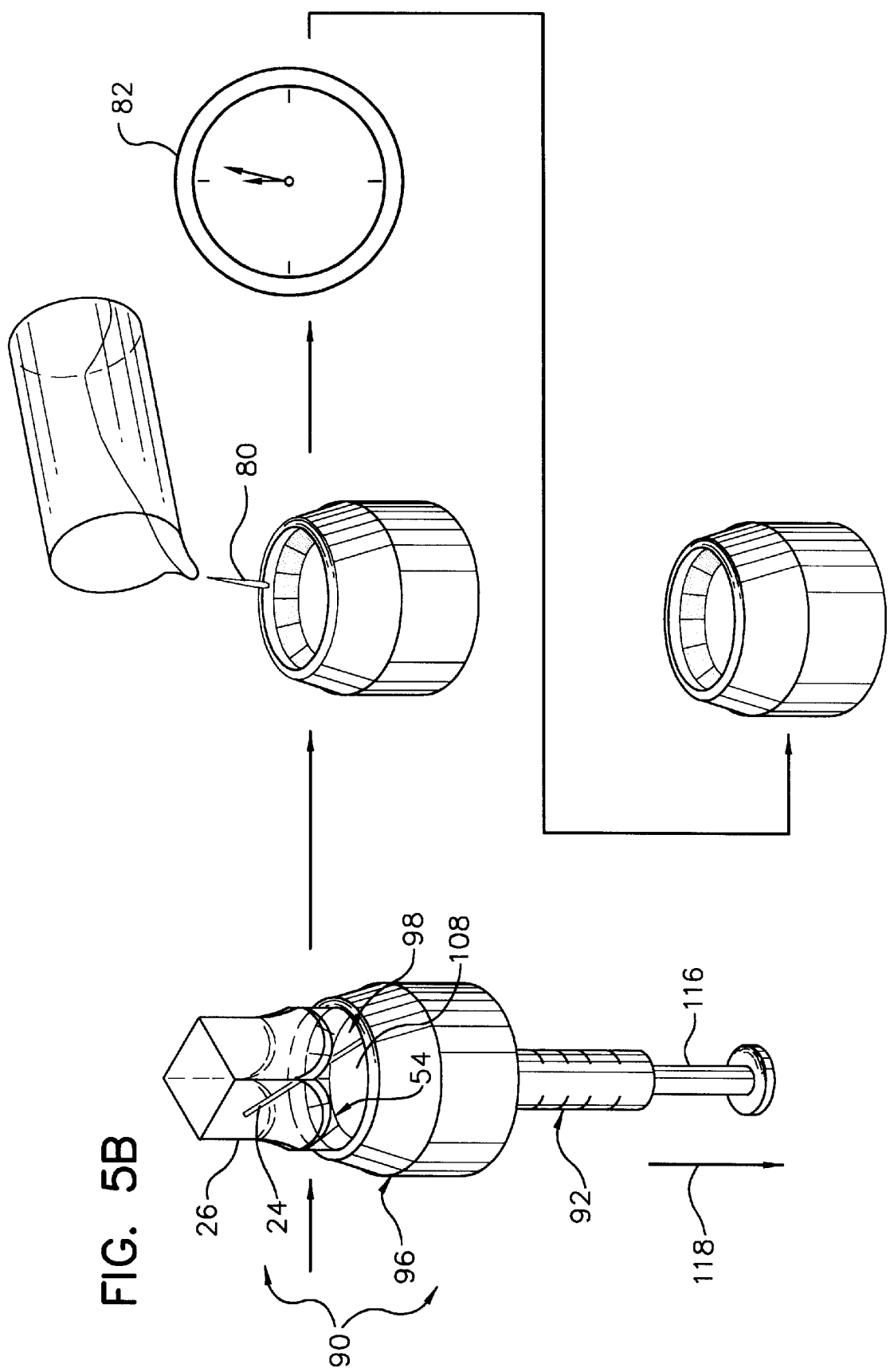
Figure 6:
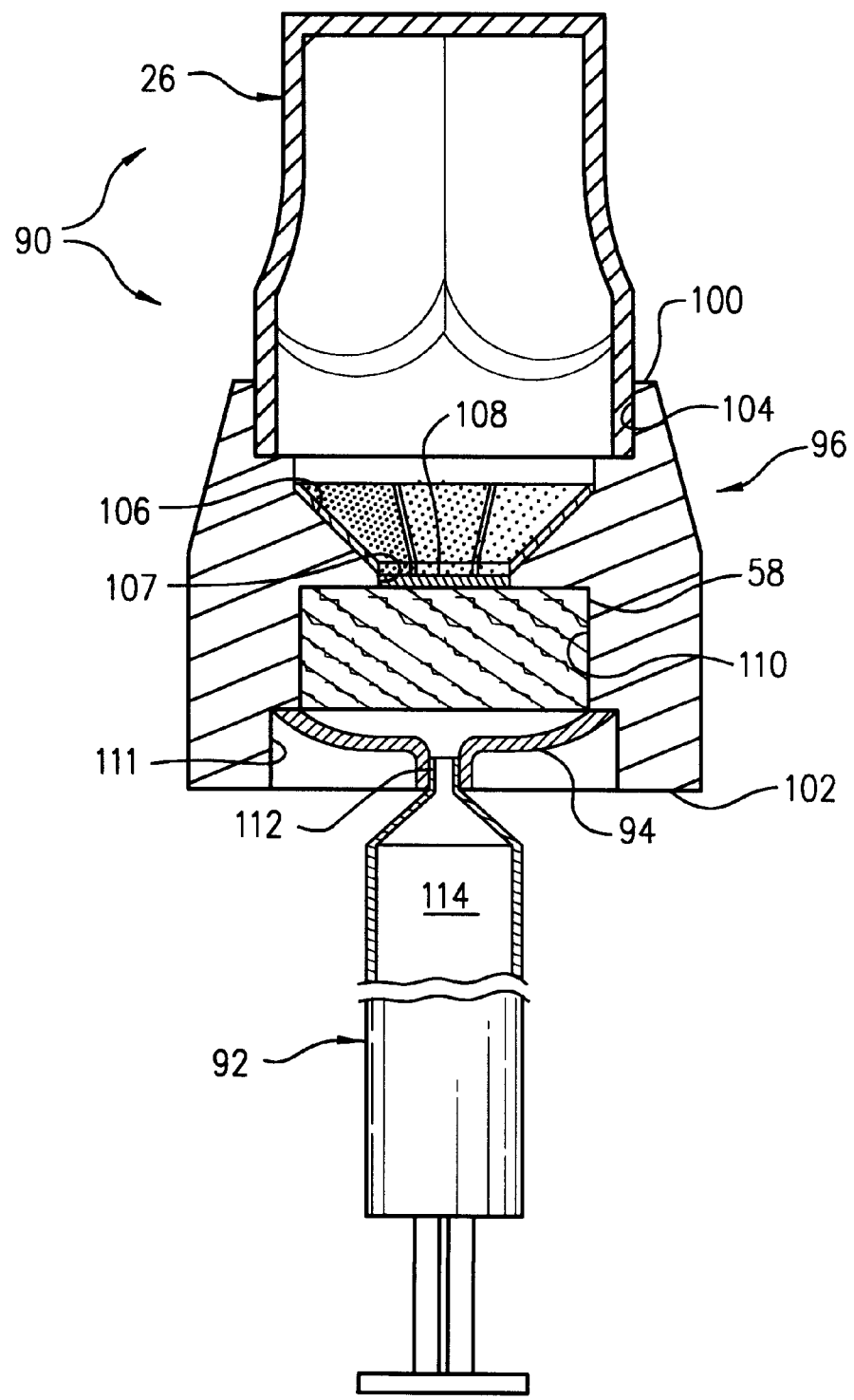
FIG. 6 is a section through a cuvette and a syringe-based assay unit employed in the kit of FIG. 4.

Referring still to the drawing, FIGS. 5A, 5B, and 6 depict the steps in a procedure for making a semiquantitative granulocyte count which differs from the procedure just described in that a diagnostic kit with a different unit for separating the granulocytes in a blood sample after a prelysing step and for making a subsequent count of the granulocytes is employed. This assay unit is identified by reference character 90.

As is shown in both FIG. 5A and FIG. 5B and in more detail in FIG. 6, assay unit 90 includes a syringe 92 with an adapter 94 and a disposable diagnostic device 96. The latter is a one-piece monolithic member typically molded from an appropriate thermo-formable polymer. A stepped central bore 98 extends through and opens onto the opposite ends 100 and 102 of this member.

The segment 104 of central bore 98 opening onto end 102 of the diagnostic device is dimensioned to complement and accept cuvette 26. Color standard 54 is housed in an adjacent, communicating segment 106 of bore 98; and, immediately below the color standard with the diagnostic device oriented as shown in FIG. 6 and in bore segment 107, is a bore spanning, porous membrane or filter 108. The next, communicating segment 110 of the bore houses absorbent block or absorber 58; and the adjacent and final segment 111 of the bore is dimensioned and configured to accept syringe adapter 94. That component is installed on the nipple 112 at the upper end of syringe 92 and in diagnostic device bore segment 111 in fluidtight relationship to the diagnostic device and syringe. It provides fluid communication between the interior 114 of the syringe and diagnostic device stepped bore 98.

The initial steps in that procedure for making a granulocyte count which employs the just-described system 90 duplicate the steps in the protocol depicted in FIGS. 1A and 1B. That is: (1) the patient's finger 30 is pricked with lance 22; (2) a quantified sample of the blood thus released is picked up with calibrated microcapillary tube 24; (3) the tube is transferred to cuvette 26; (4) the prelysing reagent 35 is added to the cuvette; (5) the lid 36 is installed; (6) the cuvette is shaken to promote disruption of the red blood cells in the sample; and (7) lid 36 is removed. Then, cuvette 26 is installed in the through bore segment 104 of diagnostic device 96 in fluidtight relationship to the diagnostic device; and the assembly of syringe 92, diagnostic device 96 and cuvette 26 is inverted (see FIGS. 5A, 5B and 6).

The next step in the procedure shown in FIGS. 5A and 5B is to withdraw the plunger 116 of syringe 92 as shown in FIGS. 5A and 5B and indicated by arrow 118 in FIG. 6. This provides a pressure differential generated force for transferring fluid—the prelysing reagent and any blood components picked up by the reagent—from cuvette 26 to diagnostic device 96 and an extremely efficient separation of this fluid from the granulocytes trapped on membrane 108. Also, the force generated by the pressure differential "fixes" the unlysed granulocytes to membrane 108 in a generally uniform distribution pattern. This is important in that the uniform distribution of the cells on membrane 108 results in a uniform as opposed to splotchy color being developed when the assay medium is subsequently added to device 26.

Thereafter, diagnostic device 96 is removed from the syringe/adapter assembly 92/94, the assay medium 80 is poured onto the granulocytes trapped on water repellent membrane 108 to release intracellular myeloperoxidase, and color is allowed to develop in this reagent for the period determined by timer 82. At the end of this period, the color of the reagent is compared to the color standard 54 in diagnostic device 96 to provide the wanted granulocyte count.

In this embodiment of the invention, the membrane 108 is fabricated from a porous water repellent material. The membrane thus effectively isolates the cells on the membrane from the absorbent material because fluids transferred to absorber 58 cannot flow back through the membrane; and a slide is therefore not necessary. Syringe 92 creates a pressure differential which overcomes the propensity of the hydrophobic membrane 108 to keep liquid from passing through it to absorber 58 at the end of the prelysing and filtration steps.

Figure 7:
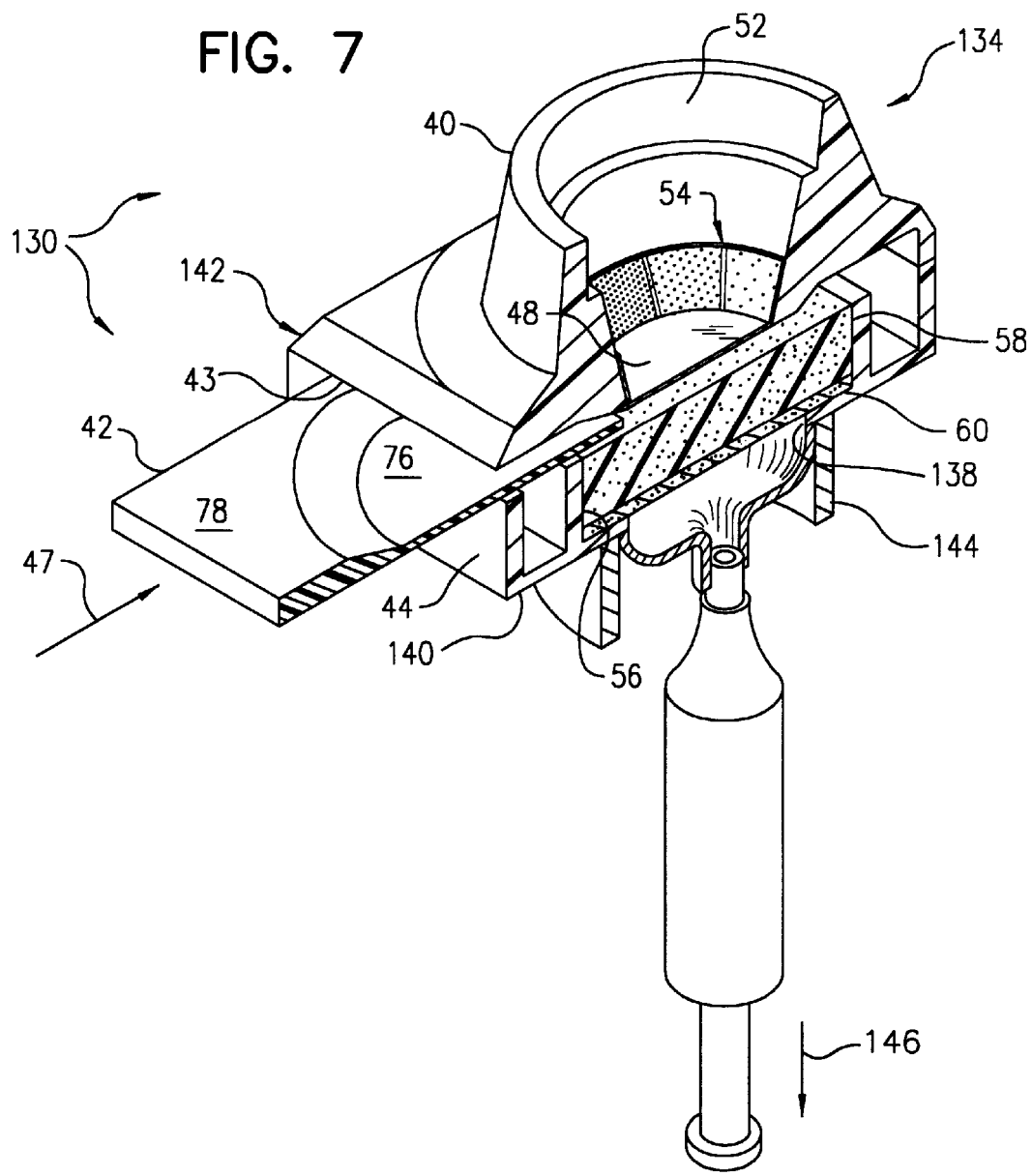
FIG. 7 is a section through a third assay unit embodying the principles of the present invention.

Referring still to the drawing, FIG. 7 depicts a syringe-based diagnostic unit 130 which includes the features of a slide-based diagnostic device such as that identified by reference character 26 in FIG. 1 and those of a syringe-based system as identified by reference character 90 in FIG. 6. System 130 thus includes a syringe 92, a diagnostic device 134 similar to the device 28 shown in FIG. 3 and an adapter 92 which provides fluid communication between the syringe and the diagnostic device.

For the most part, diagnostic devices 28 and 134 are identical; the same reference characters have been employed to identify those components and elements of the two devices which are alike.

As is apparent from FIG. 7, essentially the only difference between the two diagnostic devices 28 and 134 is that an aperture 138 is formed in the bottom wall 140 of the base 142 of diagnostic device 134; and a syringe adapter-accepting, cylindrical collar 144 is assembled to or integrally provided on bottom wall 144 in concentric relationship to the aperture.

The procedure employing system 130 to make a granulocyte count duplicates that depicted in FIGS. 1A and 1B and discussed above to the point where the contents of the cuvette 26 are transferred to the diagnostic device. In the procedure employing unit 130, the syringe is assembled to diagnostic device 134 with adapter 94 in collar 144 to provide fluid communication between the cavity 52 in the hollow boss 40 above membrane 48 and the interior 114 of syringe 92. Then, the plunger 114 of syringe 92 is displaced in the direction indicated by arrow 146 in FIG. 7. This creates a pressure differential across membrane 48: (1) providing a highly effective removal from the upper side of the membrane of the liquid phase of the cuvette contents and any substances in that phase which might interfere with an accurate granulocyte count; and (2) fixing left behind granulocytes to the membrane.

Thereafter, slide 42 is closed to isolate membrane 54 from the absorbent material 48 in which the extracted and absorbed liquid phase of the cuvette contents is trapped; and the assay medium reagent is added. Then, as in the procedures discussed above, the indicator solution is allowed to react with intracellular myeloperoxidase released by the consequent lysing of granulocytes in the blood sample for a selected period of time, and a granulocyte count is made by then comparing the color of the indicator solution with color standard 54.

Those examples which follow describe in detail particular tests in which the diagnostic procedure of the present invention was employed to determine whether granulocytes were present in a blood sample and to make granulocyte counts.

EXAMPLE I

A sample of human blood was drawn into a calibrated, siliconized microcapillary tube of known volume, thus providing a standard amount of blood to be analyzed.

The blood was quantitatively spotted onto a glass microfiber filter with a 1.2 micrometer cut-off. A Whatman™ GF/C filter was used. This filter material has the following characteristics:

Material—binder-free glass microfibers
Particle Retention—1.2 Mm
Flow Rate—10.5 sec/1.00 ml
Weight—53 g/m$^2$
Water Absorption—250 ml/m$^2$.

The filter was loaded into a syringe equipped with a supportive mesh for the filter. The syringe had a 0.5 ml capacity.

The syringe was filled to the 5 ml mark with water. As discussed above, water disrupts red cells while leaving granulocytes intact.

The plunger of the syringe was depressed to exert pressure on the sample and promote dissolution of the erythrocytes in the sample by a "pressure wash" and to expel the solubilized contents of the erythrocytes.

The glass microfiber filter with its burden of unlysed granulocytes was transferred to a clean, dry surface; and five drops (or approximately 250 microliters) of a test reagent solution or assay medium was added. The test reagent solution was prepared by combining 0.5 ml of a 0.1 molar, citrate buffer of pH 5; 50 µl of granulocyte lysing and myeloperoxidase releasing 0.1% Triton X-100™ detergent; 300 µl of 100 millimolar, aqueous, 3-amino-1,2,4 triazole; 50 µl of 0.01% hydrogen peroxide; 50 µl of 10 mg per ml aqueous o-tolidine; and 50 µl of $H_2O$. This yielded 1.0 ml of a test reagent solution with the following final concentrations: phosphate buffer, 50 mM; Triton X-100™, 0.005%; 3-amino-1,2,4 triazole, 30 mM; hydrogen peroxide, 0.0005%; and o-tolidine, 0.5 mg per ml.

After 30 seconds, that area of the microfiber filter spotted with the blood sample turned blue. This was an indication that granulocytes were present in the blood sample.

Figure 4:
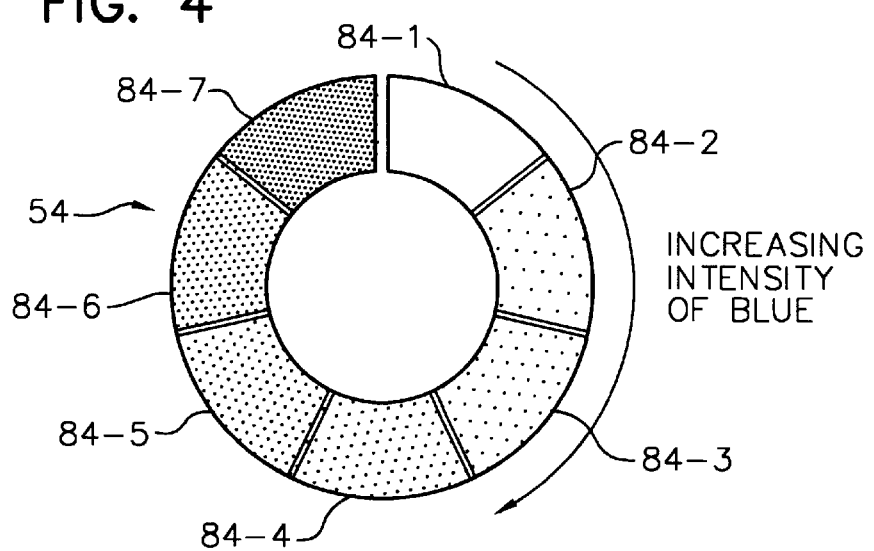
FIG. 4 shows, in detail, a color standard incorporated in the assay device.

The intensity of the color was related to granulocyte count with a color standard as shown in FIG. 4 to obtain an at least semiquantitative granulocyte count.

EXAMPLE II

The procedure described in EXAMPLE I was repeated, using a reagent solution or assay medium which differed from that described in EXAMPLE I in the following respects: (1) the solution was buffered with a phosphate buffer; and (2) the final concentration of the o-tolidine in the test reagent solution was 0.2 mg per ml.

The color development was assessed 5 minutes after the addition of the assay medium to the spotted blood sample.

The development of color over a longer period of time provides greater resolution and therefore a more accurate granulocyte account in those circumstances where the blood sample has a high granulocyte count. That is, in this circumstance, the appearance of the indicator solution after being developed over a short period of time by two samples with high but significantly different granulocyte counts may be indistinguishable because the color develops so rapidly in both cases. By spreading the color development over a longer period of time so that the color will develop slower, the color in the sample with the lower granulocyte count will not have developed to the same intensity level as the color in the sample with the higher granulocyte count at the end of the color development step; and the two samples can therefore be distinguished between.

EXAMPLE III

The procedure described in EXAMPLE I was employed with the following changes: the volume of the blood sample was 25 µl rather than 10 µl; and the blood was transferred to a Pre-Sep glass prefilter G-15™ (Micron Separation, Inc.). The blood laden filter was then transferred to a vial, and 2 ml of the test reagent solution was added. The resulting color development was measured after 5 minutes.

EXAMPLE IV

The procedure of EXAMPLE I was repeated, using five drops of a test reagent solution prepared by combining 875 microliters of 0.1 molar, pH 5 citrate buffer; 100 microliters of 0.1% Triton X-100™ detergent; 125 microliters of 1 millimolar ascorbic acid (prepared in a citrate buffer); 100 microliters of 0.01% $H_2O_2$; 600 microliters of 100 millimolar 3-amino-1,2,4-triazole; and 200 microliters of 10 mg per ml aqueous o-tolidine. This yielded 2.0 ml of a test reagent solution with the following final concentrations: citrate buffer, 50 mM; Triton X-100™, 0.005%; ascorbic acid, 62.5 mM; $H_2O_2$, 0.0005%; 3-amino-1,2,4 triazole, 30 mM; o-tolidine, 1 mg per ml. The color development was measured after 30 seconds, 1 minute and 2 minutes.

EXAMPLE V

The procedure elucidated in EXAMPLE I was repeated with the following changes: (1) the buffer was 970 μl of 0.1 molar, pH 5 citrate; and (2) the volume of 1 millimolar ascorbic acid was decreased to 30 microliters (the final concentration of ascorbic acid was 15 millimolar).

The blue color which developed in that area of the filter on which the blood sample had been spotted was assessed after one minute. The intensity was less than that of the reference standard. This meant that the white cell count of the sample was less than 2500 granulocytes per liter of blood.

EXAMPLE VI

The procedure described in EXAMPLE I was repeated with the following changes: (1) 1 ml of 0.1 molar, pH 6.5 phosphate buffer was used in the test reagent solution; (2) the volume of the one millimolar ascorbic acid was decreased to 25 microliters (for a final concentration of 12.5 millimolar); (3) the volume of the o-tolidine was decreased to 100 microliters (for a final concentration of 0.5 mg per ml); and (4) 75 microliters of $H_2O$ was added to bring the final volume of the assay medium to 2.0 ml.

The resulting color, assessed at 1 minute, was less intense than the blue reference. That signified a count of less than 2500 granulocytes per microliter in the blood sample.

The efficacy of the present invention has also been clinically demonstrated. Two different tests were employed, one to detect low granulocyte levels (less than 2.5 [all granulocyte counts given as thousands cells/mm$^3$]) and the other to estimate the level of granulocytes (given as a range only [i.e. less than 2, 2–5, 5–10, greater than 10] since the test is not strictly quantitative).

Blood samples were received from various institutions and assayed. The results of the assay were compared to actual neutrophil counts as determined by a Coulter counter. The blood samples were obtained by venipuncture, using Vacutainer brand tubes with $K_3$EDTA as an anticoagulant. The samples were stored at approximately 5° C. until assayed (usually on the day after the sample was drawn).

EXAMPLE VII

Detection of Granulocyte Levels Less Than 2.5

The blood sample was mixed well. Then a 10 microliter aliquot of blood was spotted (using a digital microliter pipette) onto a Whatman GF/C glass microfiber filter (pore size 1.2 micron) that had been dipped in double distilled water, blotted slightly and placed on the sintered glass disk of a Millipore filtration apparatus. A glass tube was then clamped on top of the sintered glass disk so that the filter was held in place and no fluid could escape around the edges of the filter. Approximately 2 ml of double distilled water was added to the glass tube. The entire apparatus was then shaken for about 10 seconds to suspend the blood sample and lyse the red cells. Then vacuum was applied under the sintered glass disk to remove the fluid. This lysing step was repeated once; then the filter was transferred to a glass microscope slide (all handling of the filter was done with forceps). Five to seven drops of an indicator reagent solution or assay medium were added to the filter; and, one minute after this addition, color development was scored using a color standard like that shown in FIG. 4 but with six different intensities of blue (numbered 1 through 6 from palest blue to most intense blue).

If the color development was four or more at one minute, the sample was considered to have a granulocyte level greater than 2.5; if the color development was three or less at one minute, the sample had a granulocyte level of less than 2.5; if the color development appeared to be between three and four, the test was considered inconclusive (most of these samples had granulocyte counts close to 2.5 and were therefore borderline).

The test solution contained the following: citrate buffer (50 mM, pH 5.0), ascorbic acid (15 mM), Triton X-100 (0.005%), hydrogen peroxide (0.0005% in one test and 0.000625% in a later test, both based on the assumption that the stock solution was 30%), aminotriazole (30 mM) and o-tolidine (1 mg/ml).

Twenty-five samples had actual neutrophil counts of 2.5 or less as measured with the Coulter counter. Using the procedure of the present invention, 8 of these were identified as having granulocyte levels less than 2.5; 16 were considered borderline; and one (actual neutrophil count 2.4) was considered greater than 2.5 (this sample was later repeated and found to be borderline).

Figure 8:
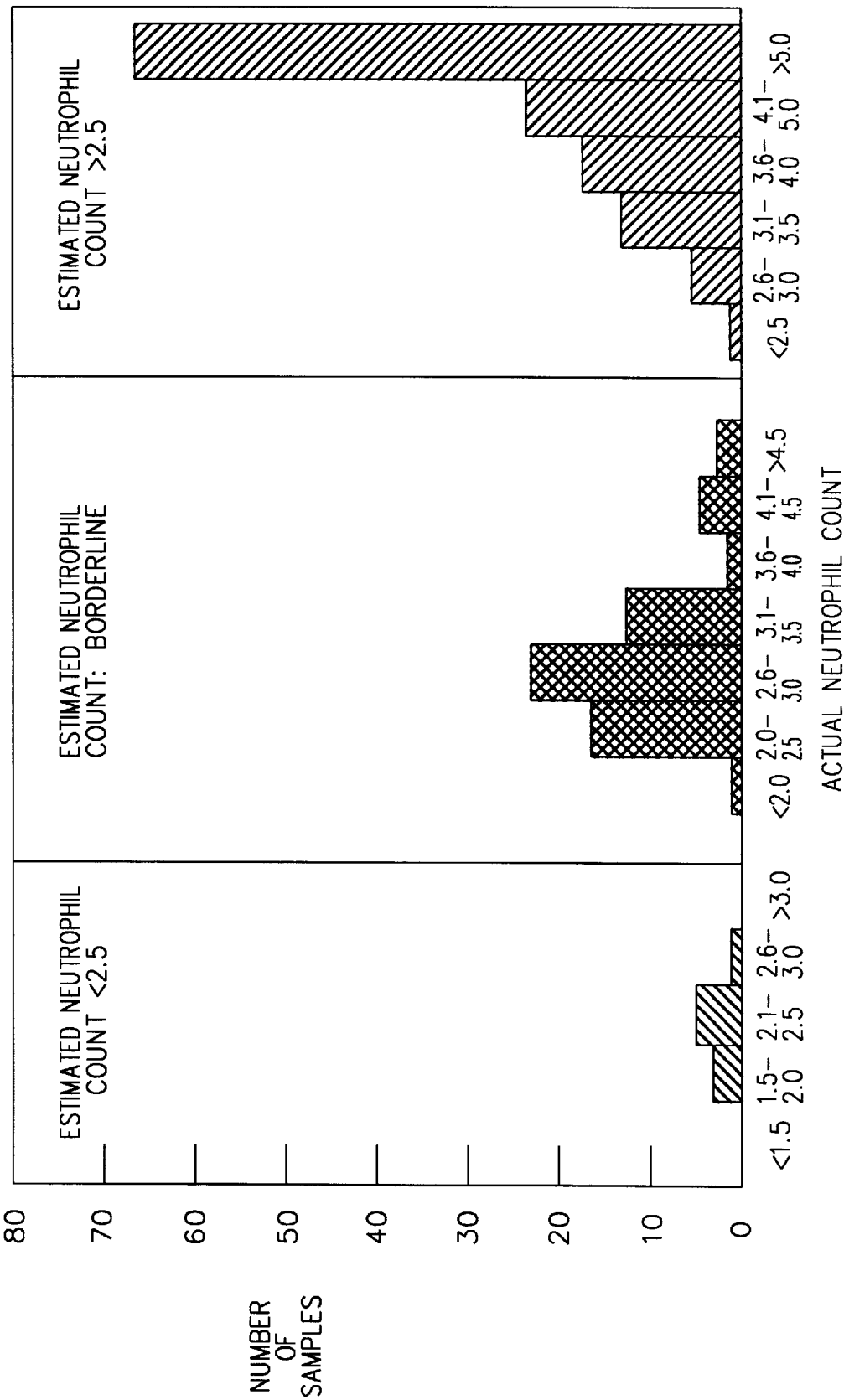
FIG. 8 is a bar chart summarizing the results obtained in one study in which granulocytes were detected with a process embodying the principles of the present invention.

One sample testing less than 2.5 was actually slightly higher (2.8). Of the remaining 172 samples, 44 tested as borderline; 23 had neutrophil counts of 2.6 to 3.0; 11 were between 3.1 and 3.5; 2 were between 3.6 and 4.0; 5 were between 4.0 and 5.0; and 3 were greater than 5.0 (repeat assays of these placed them in the greater than 2.5 category). The remaining 128 samples tested as having neutrophil levels greater than 2.5. Six had neutrophil counts between 2.5 and 3.0, and 122 had neutrophil counts greater than 3.0 (see Table 1 and FIG. 8).

TABLE 1

Detection of Neutrophil Levels Less than 2.5

| Sample No. | Color Score | Interpretation | Neutrophil Count |
|---|---|---|---|
| 1 | 4+ | > | 3.5 |
| 2 | 3+ | BL | 2.0 |
| 3 | 4 | > | 3.9 |
| 4 | 3+ | BL | 3.0 |
| 5 | 3+ | BL | 3.0 |
| 6 | 4+ | > | 4.3 |
| 7 | 4− | BL | 2.7 |
| 8 | 5 | > | 6.7 |
| 9 | 5 | > | 4.9 |
| 10 | 4+ | > | 5.6 |
| 11 | 4 | > | 5.9 |
| 12 | 3+ | BL | 2.5 |
| 13 | 4+ | > | 5.4 |
| 14 | 5 | > | 7.9 |
| 15 | 4− | BL | 2.9 |
| 16 | 5 | > | 3.8 |
| 17 | 3+ | BL | 3.2 |
| 18 | 4+ | > | 4.7 |
| 19 | 4 | > | 5.5 |
| 20 | 4+ | > | 4.1 |
| 22 | 4+ | > | 7.7 |
| 23 | 4 | > | 4.1 |
| 24 | 3 | < | 2.5 |
| 25 | 6 | > | 12.7 |

TABLE 1-continued

Detection of Neutrophil Levels Less than 2.5

| Sample No. | Color Score | Interpretation | Neutrophil Count |
|---|---|---|---|
| 27 | 4+ | > | 9.4 |
| 28 | 5 | > | 8.6 |
| 29 | 4+ | > | 6.9 |
| 30 | 5 | > | 8.3 |
| 31 | 3− | < | 1.7 |
| 32 | 4 | > | 7.3 |
| 32R | 4 | > | 7.3 |
| 33 | 3 | < | 2.3 |
| 34 | 4 | > | 3.3 |
| 35 | 3 | < | 2.3 |
| 36 | 4 | > | 3.7 |
| 37 | 4 | > | 5.3 |
| 38 | 4 | > | 3.6 |
| 39 | 4− | BL | 3.0 |
| 40 | 5 | > | 6.1 |
| 41 | 3+ | BL | 2.8 |
| 42 | 4− | BL | 3.6 |
| 43 | 3+ | BL | 2.4 |
| 44 | 4− | BL | 2.9 |
| 45 | 4 | > | 3.2 |
| 46 | 4 | > | 3.4 |
| 47 | 4 | > | 3.1 |
| 48 | 4 | > | 2.8 |
| 49 | 4 | > | 4.0 |
| 50 | 4 | > | 3.9 |
| 51 | 4+ | > | 6.0 |
| 52 | 4 | > | 5.2 |
| 53 | 3+ | BL | 3.0 |
| 54 | 4− | BL | 5.5 |
| 54R | 4 | > | 5.5 |
| 55 | 4 | > | 3.4 |
| 56 | 5 | > | 5.7 |
| 57 | 4 | > | 3.1 |
| 58 | 3+ | BL | 2.9 |
| 59 | 4 | > | 3.7 |
| 60 | 4+ | > | 7.8 |
| 61 | 4 | > | 3.7 |
| 62 | 4− | BL | 2.5 |
| 63 | 4 | > | 3.3 |
| 64 | 3+ | BL | 2.7 |
| 65 | 3+ | > | 8.3 |
| 66 | 5 | > | 8.1 |
| 67 | 4 | > | 3.8 |
| 68 | 4 | > | 4.8 |
| 69 | 4 | > | 3.7 |
| 70 | 3+ | BL | 3.1 |
| 71 | 4+ | > | 6.7 |
| 72 | 4 | > | 3.7 |
| 73 | 4 | > | 5.2 |
| 74 | 4 | > | 4.0 |
| 75 | 4− | BL | 3.0 |
| 76 | 3+ | BL | 4.3 |
| 77 | 3− | < | 1.8 |
| 78 | 5 | > | 7.3 |
| 79 | 5+ | > | 10.3 |
| 80 | 3 | < | 1.7 |
| 81 | 5+ | > | 10.7 |
| 82 | 5 | > | 11.3 |
| 83 | 4− | BL | 3.2 |
| 84 | 4 | > | 4.0 |
| 85 | 3+ | BL | 1.9 |
| 86 | 5 | > | 7.7 |
| 87 | 4,4+ | > | 6.5 |
| 88 | 4+ | > | 6.7 |
| 89 | 3+ | BL | 2.4 |
| 90 | 4 | > | 5.1 |
| 91 | 4 | > | 6.9 |
| 92 | 4− | BL | 2.8 |
| 93 | 5+ | > | 8.0 |
| 93R | 5+ | > | 8.0 |
| 94 | 3+ | BL | 2.2 |
| 95 | 4− | BL | 5.5 |
| 95R | 4 | > | 5.5 |
| 96 | 3+ | BL | 2.0 |
| 97 | 4+ | > | 8.6 |
| 98 | 5 | > | 10.5 |
| 99 | 4− | BL | 1.9 |
| 100 | 4+ | > | 3.8 |
| 100R | 4+ | > | 3.8 |
| 101 | 3+ | BL | 2.3 |
| 102 | 4 | > | 4.5 |
| 103 | 4 | > | 4.2 |
| 104 | 5 | > | 5.8 |
| 105 | 3+ | BL | 2.2 |
| 106 | 4 | > | 3.5 |
| 107 | 4+ | > | 4.1 |
| 108 | 5 | > | 5.5 |
| 109 | 4 | > | 3.4 |
| 110 | 3+ | BL | 3.0 |
| 111 | 4,3+ | BL | 3.0 |
| 112 | 4+ | > | 6.3 |
| 113 | 4 | > | 3.1 |
| 114 | 4 | > | 3.0 |
| 115 | 4 | > | 3.6 |
| 116 | 4 | > | 4.5 |
| 116R | 4 | > | 4.5 |
| 117 | 5 | > | 5.3 |
| 118 | 4− | BL | 2.8 |
| 119 | 4,3+ | BL | 3.4 |
| 120 | 4,4− | BL | 2.8 |
| 121 | 5 | > | 4.9 |
| 122 | 5 | > | 4.0 |
| 122R | 4+ | > | 4.0 |
| 123 | 4 | > | 2.8 |
| 124 | 5 | > | 5.7 |
| 125 | 4 | > | 4.3 |
| 126 | 4 | > | 4.0 |
| 127 | 4 | > | 3.4 |
| 128 | 4+ | > | 5.1 |
| 129 | 5+ | > | 7.3 |
| 130 | 4+ | > | 4.1 |
| 131 | 5 | > | 6.2 |
| 131R | 4+ | > | 6.2 |
| 132 | 5 | > | 3.8 |
| 133 | 4 | > | 4.4 |
| 134 | 5 | > | 7.0 |
| 134R | 5 | > | 7.0 |
| 135 | 3+ | BL | 3.1 |
| 136 | 4 | > | 4.2 |
| 137 | 4 | > | 4.6 |
| 138 | 3+ | BL | 3.6 |
| 139 | 4 | > | 4.3 |
| 140 | 4 | > | 4.4 |
| 141 | 4− | BL | 4.1 |
| 142 | 3+ | BL | 2.2 |
| 143 | 3+ | BL | 2.0 |
| 144 | 4 | > | 2.6 |
| 145 | 4 | BL | 2.7 |
| 146 | 4,4 | BL | 2.4 |
| 147 | 4− | BL | 2.0 |
| 148 | 4 | > | 2.9 |
| 149 | 6,5+ | > | 6.3 |
| 150 | 4+,5 | > | 5.3 |
| 151 | 4− | BL | 2.4 |
| 152 | 4 | > | 2.6 |
| 153 | 6 | > | 9.6 |
| 154 | 3+ | BL | 4.4 |
| 155 | 4+ | > | 5.0 |
| 156 | 5 | > | 5.3 |
| 157 | 4 | > | 3.3 |
| 158 | 4+,5 | > | 7.8 |
| 159 | 3+ | BL | 3.1 |
| 160 | 5 | > | 5.6 |
| 161 | 3+ | BL | 2.9 |
| 162 | 4+ | > | 5.0 |
| 163 | 6 | > | 10.7 |
| 164 | 6 | > | 6.8 |
| 164R | 6 | > | 6.8 |

TABLE 1-continued

Detection of Neutrophil Levels Less than 2.5

| Sample No. | Color Score | Interpretation | Neutrophil Count |
|---|---|---|---|
| 165 | 4 | > | 3.2 |
| 166 | 3+ | BL | 2.2 |
| 167 | 4−,3+ | BL | 3.2 |
| 168 | 5−,4+ | > | 7.4 |
| 169 | 4 | > | 4.4 |
| 170 | 4+,5 | > | 5.7 |
| 171 | 4− | BL | 3.0 |
| 172 | 3+,4− | BL | 2.7 |
| 173 | 4 | > | 2.4 |
| 173R | 3+ | BL | 2.4 |
| 174 | 4 | > | 4.2 |
| 175 | 5 | > | 5.6 |
| 176 | 3 | < | 2.1 |
| 177 | 4+ | > | 8.7 |
| 178 | 6 | > | 7.0 |
| 179 | 3,3− | < | 2.1 |
| 180 | 3+ | BL | 3.3 |
| 181 | 4 | > | 3.9 |
| 182 | 5 | > | 6.6 |
| 183 | 4 | > | 4.4 |
| 184 | 3+ | BL | 3.3 |
| 185 | 4 | > | 7.0 |
| 186 | 3 | < | 2.8 |
| 187 | 4 | > | 5.1 |
| 188 | 4 | > | 5.4 |
| 189 | 3+ | BL | 3.4 |
| 190 | 3+ | BL | 6.9 |
| 190R | 4 | > | 6.9 |
| 191 | 4 | > | 6.3 |
| 191R | 3 | < | 6.3 |
| 192 | 3+ | BL | 4.2 |
| 193 | 4 | > | 6.0 |
| 193R | 4 | > | 6.0 |
| 194 | 4 | > | 5.3 |
| 195 | 4 | > | 6.5 |
| 195R | 4 | > | 6.5 |
| 196 | 3+ | BL | 4.3 |
| 197 | 3+ | BL | 3.0 |
| 198 | 3+ | BL | 3.4 |
| 199 | 5 | > | 8.9 |
| 199R | 5−,5 | > | 8.9 |
| 200 | 3+ | BL | 2.6 |

> = greater than 2.5 thousand cells/mm$^3$
< = less than 2.5 thousand cells/mm$^3$
BL = borderline
R = repeated sample
$^1$ = as determined with the Coulter counter

EXAMPLE VIII

Estimation of Granulocyte Levels

Blood samples obtained as described above were treated with a test solution containing 50 mM OF pH 5.0 citrate buffer, 62.5 $\mu$M ascorbic acid, 0.005% Triton X-100™, 30 mM aminotriazole, 1 mg/ml o-tolidine and 0.0005% hydrogen peroxide (assuming that the stock solution of hydrogen peroxide was 30%). Color development was scored at 30 seconds, 1 minute and 2 minutes after the test solution had been added. Each sample was assigned to one of four ranges of neutrophil counts (>2, 2–5, 5–10 and >10) based on the following:

i. color≧3 at 30 seconds=neutrophil count>10 ii. color<3 at 30 seconds, ≧3 at 1 minute=neutrophil count of 2–5 iii. color<3 at 30 seconds and 1 minute, ≧3 at 2 minutes= neutrophil count of 2–5 iv. color<3 at 2 minutes=neutrophil count<2.

Ranges iii and iv were refined by considering the intensity of color development at the time immediately preceding that at which the color score was 3 or more. Thus, if the sample was assigned to the 5–10 range and had a color score of 2+ or 3− at 30 seconds, it would probably be near the high end of the range. A color score of 1+ at 30 seconds would suggest that the neutrophil count fell in the low end of the range. Similarly, in the 2–5 range, a color score of 2+ or 3− at 1 minute would indicate the sample was probably at the high end of the range; and a color score of 1+ would suggest the neutrophil count was near the low end of the range.

Figure 9:
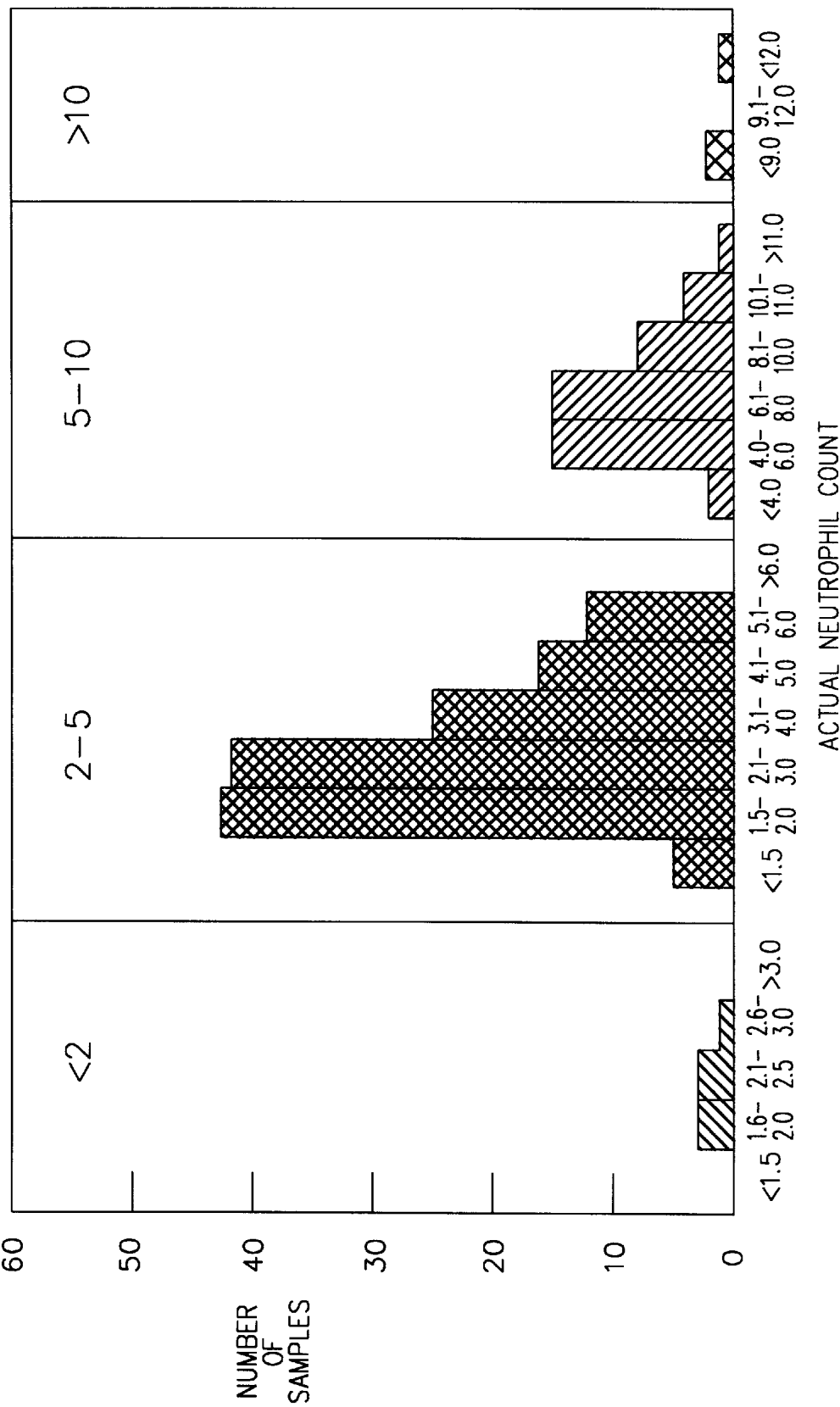
FIG. 9 is a bar chart summarizing the results of a second study in which granulocyte levels were determined by employing a variation of the procedure used in the first study.

Using this method of estimating neutrophil counts, 7 samples were designated as less than 2. Three of these were between 1.5 and 2.0, 3 were between 2.1 and 2.5, and one was between 2.6 and 3.0. No samples with neutrophil counts greater than 3 were assigned to this range. One hundred forty-three samples were designated as having neutrophil counts of between 2 and 5. Five of these had actual neutrophil counts of 1.5–2.0, 43 were between 2.1 and 3.0, 42 were between 3.1 and 4.0, 25 were between 4.1 and 5.0, 16 were between 5.1 and 6.0 and 12 were over 6.0. Forty-five samples were estimated as having neutrophil counts of between 5 and 10. Actual neutrophil counts of these were: less than 4 (2 samples), between 4.0 and 6.0 (15 samples), between 6.1 and 8.0 (15 samples), between 8.1 and 10.0 (8 samples), between 10.1 and 11.0 (4 samples), and greater than 11.0 (1 sample). The neutrophil counts of the remaining 3 samples were estimated as greater than 10. Two of these had actual counts of less than 10 (8.0 and 6.8), and one was greater than 10 (12.7) (see Table 2 and FIG. 9).

TABLE 2

Estimate of Neutrophil Levels

| Sample Number | Color Source | | | Estimated Neutrophil | |
|---|---|---|---|---|---|
| | 30 sec | 1 min | 2 min | Range | Count |
| 1 | 1+ | 2− | 4 | 2–5 | 3.5 |
| 2 | 1+ | 1+ | 3+ | 2–5L | 2.0 |
| 3 | 1+ | 2 | 4 | 2–5 | 3.9 |
| 4 | 1+ | 2− | 3+ | 2–5 | 3.0 |
| 5 | 1+ | 1+ | 3+ | 2–5L | 3.0 |
| 6 | 1+ | 3− | 4 | 5–10L | 4.3 |
| 7 | 1+ | 2− | 4− | 2–5 | 2.7 |
| 8 | 1+ | 3 | 4 | 5–10L | 6.7 |
| 9 | 1+ | 2+,3− | 4 | 2–5H | 4.9 |
| 10 | 1+ | 3 | 4 | 5–10L | 5.6 |
| 11 | 1+ | 2+ | 4 | 2–5H | 5.9 |
| 12 | 1+ | 1+ | 3+ | 2–5L | 2.5 |
| 13 | 1+ | 2+,3− | 4− | 2–5H | 5.4 |
| 14 | 1+ | 3− | 4+ | 5–10L | 7.9 |
| 15 | 1+ | 2 | 3+ | 2–5 | 2.9 |
| 16 | 1+ | 3 | 4+ | 5–10L | 3.8 |
| 17 | 1+ | 2+ | 3+ | 2–5H | 3.2 |
| 18 | 1+ | 3 | 4+ | 5–101 | 4.7 |
| 19 | 1+ | 2+,3− | 4 | 2.5H | 5.5 |
| 20 | 1+ | 2+,3− | 4 | 2.5H | 4.1 |
| 22 | 2− | 4− | 4− | 5.10 | 7.7 |
| 23 | 1+ | 2+ | 4− | 2–5H | 4.1 |
| 24 | 1+ | 1+ | 3+ | 2–5L | 2.5 |
| 25 | 3− | 4 | 6 | >10 | 12.7 |
| 27 | 1+ | 2+,3− | 4− | 5–10L | 9.4 |
| 28 | 2− | 3+ | 4 | 5–10 | 8.6 |
| 29 | 2 | 3− | 4 | 5–10 | 6.9 |
| 30 | 1+ | 3− | 4 | 5–10L | 8.3 |
| 31 | 1+ | 1+ | 2+ | <2 | 1.7 |
| 32 | 1+ | 2 | 3+ | 2–5 | 7.3 |
| 32R | 1+ | 3− | 4 | 5–10L | 7.3 |
| 33 | 1+ | 1+ | 2+ | <2 | 2.3 |
| 34 | 1+ | 2 | 3+ | 2–5 | 3.3 |
| 35 | 1+ | 1+ | 3− | <2 | 2.3 |
| 36 | 1+ | 2− | 3+ | 2–5 | 3.7 |

TABLE 2-continued

Estimate of Neutrophil Levels

| Sample Number | Color Source 30 sec | 1 min | 2 min | Estimated Neutrophil Range | Count |
|---|---|---|---|---|---|
| 37 | 1+ | 2 | 3+ | 2–5 | 5.3 |
| 38 | 1+ | 2 | 3+ | 2.5 | 3.6 |
| 39 | 1+ | 2– | 3+ | 2–5 | 3.0 |
| 40 | 1+ | 2+ | 4– | 2–5H | 6.1 |
| 41 | 1+ | 1+ | 3 | 2–5L | 2.8 |
| 42 | 1+ | 2– | 3 | 2–5 | 3.6 |
| 43 | 1+ | 2 | 3 | 2–5 | 2.4 |
| 44 | 1+ | 1+ | 3 | 2–5L | 2.9 |
| 45 | 1+ | 2 | 4– | 2–5 | 3.2 |
| 46 | 1+ | 2 | 3+ | 2–5 | 3.4 |
| 47 | 1+ | 2+ | 3+ | 2–5H | 3.1 |
| 48 | 1+ | 2+ | 3+ | 2–5H | 2.8 |
| 49 | 1+ | 2 | 3+ | 2–5 | 4.0 |
| 50 | 2– | 2+ | 4– | 2–5H | 3.9 |
| 51 | 2– | 3– | 4 | 5–10 | 6.0 |
| 52 | 1+ | 2 | 4– | 2–5 | 5.2 |
| 53 | 1+ | 2 | 3+ | 2–5 | 3.0 |
| 54 | 1+ | 1 | 3+ | 2–5 | 5.5 |
| 54R | 1+ | 2+ | 3+ | 2–5H | 5.5 |
| 55 | 1+ | 2 | 3 | 2–5 | 3.4 |
| 56 | 2– | 3 | 4 | 5–10 | 5.7 |
| 57 | 1+ | 2 | 3+ | 2–5 | 3.1 |
| 58 | 1+ | 2 | 3+ | 2–5 | 2.9 |
| 59 | 1+ | 2 | 3+ | 2–5 | 3.7 |
| 60 | 2– | 3– | 4– | 5–10 | 7.8 |
| 61 | 1+ | 2 | 4– | 2–5 | 3.7 |
| 62 | 1+ | 2–,1+ | 3 | 2–5L | 2.5 |
| 63 | 1+ | 2 | 3+ | 2–5 | 3.3 |
| 64 | 1+ | 1+ | 3 | 2–5L | 2.7 |
| 65 | 1+,2– | 3– | 4 | 5–10 | 8.3 |
| 66 | 2 | 3– | 4– | 5–10 | 8.1 |
| 67 | 1+ | 2 | 3+ | 2–5 | 3.8 |
| 68 | 1+ | 2+ | 3+ | 2–5H | 4.8 |
| 69 | 1+ | 2 | 4– | 2–5 | 4.7 |
| 70 | 1+ | 2– | 3+ | 2–5 | 3.1 |
| 71 | 2– | 2+,3– | 4– | 2–5H | 6.7 |
| 72 | 1+ | 2 | 3+ | 2–5 | 3.7 |
| 73 | 1+ | 2 | 3+ | 2–5 | 5.2 |
| 74 | 1+ | 2 | 3+ | 2–5 | 4.0 |
| 75 | 1+ | 2– | 3– | 2–5 | 3.0 |
| 76 | 1+ | 2 | 3+ | 2–5 | 4.3 |
| 77 | 1+ | 1+ | 2 | <2 | 1.8 |
| 78 | 2 | 3+ | 4 | 5–10 | 7.3 |
| 79 | 2 | 3+ | 4+ | 5–10 | 10.3 |
| 80 | 1+ | 1+ | 2+ | <2 | 1.7 |
| 81 | 2+ | 3+,4– | 5 | 5–10H | 10.7 |
| 82 | 2+ | 4– | 5– | 5–10H | 11.3 |
| 83 | 1+ | 2 | 3+ | 2–5 | 3.2 |
| 84 | 1+ | 2+ | 4– | 2–5H | 4.0 |
| 85 | 1+ | 2 | 3+ | 2–5 | 2.9 |
| 86 | 2 | 3 | 4 | 5–10 | 7.7 |
| 87 | 2 | 3 | 4– | 5–10 | 6.5 |
| 88 | 2– | 2+,3– | 4 | 2–5H | 6.7 |
| 89 | 1+ | 2– | 3 | 2–5 | 2.4 |
| 90 | 1+ | 2,2+ | 3+,4– | 2–5H | 5.1 |
| 91 | 2 | 3 | 4 | 5–10 | 6.9 |
| 92 | 1+ | 2,2+ | 3+ | 2–5 | 2.8 |
| 93 | 3 | 4 | 5– | >10 | 8.0 |
| 93R | 3 | 4 | 5 | >10 | 8.0 |
| 94 | 1+ | 2 | 3 | 2–5 | 2.2 |
| 95 | 1+ | 1+ | 3+ | 2–5H | 5.5 |
| 95R | 1+ | 2– | 4–,3+ | 2–5 | 5.5 |
| 96 | 1+ | 2 | 3 | 2–5 | 2.0 |
| 97 | 2 | 3,3– | 4 | 5–10 | 8.6 |
| 98 | 2 | 3+ | 4 | 5–10 | 10.5 |
| 99 | 1+ | 2– | 3 | 2–5 | 1.9 |
| 100 | 2 | 3– | 4 | 5–10 | 3.8 |
| 100R | 2 | 3 | 4 | 5–10 | 3.8 |
| 101 | 1+ | 1+ | 3 | 2–5L | 2.3 |
| 102 | 1+ | 2 | 3+ | 2–5 | 4.5 |
| 103 | 1+ | 2 | 3+ | 2–5 | 4.2 |
| 104 | 2 | 3 | 4+ | 5–10 | 5.8 |
| 105 | 1+ | 1+ | 3 | 2–5L | 2.2 |
| 106 | 1+ | 2 | 4– | 2–5 | 3.5 |
| 107 | 2– | 3 | 4 | 5–10 | 4.1 |
| 108 | 2– | 3– | 4 | 5–10 | 5.5 |
| 109 | 1+ | 1 | 4– | 2–5 | 3.4 |
| 110 | 1+ | 2 | 3+ | 2–5 | 3.0 |
| 111 | 1+ | 1+,2– | 3 | 2–5 | 3.0 |
| 112 | 1+ | 2+,3– | 4 | 2–5H | 6.3 |
| 113 | 1+ | 2+ | 4– | 2–5H | 3.1 |
| 114 | 1+ | 2 | 3+ | 2–5 | 3.0 |
| 115 | 1+ | 2– | 3+ | 2–5 | 3.6 |
| 116 | 1+ | 2 | 3 | 2–5 | 4.5 |
| 116R | 1+ | 2+ | 4–,3+ | 2–5H | 4.5 |
| 117 | 1+,2– | 3– | 4– | 5–10L | 5.3 |
| 118 | 1+ | 1+,2– | 3 | 2–5 | 2.8 |
| 119 | 1+ | 2 | 3+ | 2–5 | 3.4 |
| 120 | 1+ | 2 | 3+ | 2–5 | 2.8 |
| 121 | 2– | 3 | 4 | 5–10 | 4.9 |
| 122 | 2,2– | 3– | 4 | 5–10 | 4.0 |
| 122R | 2– | 3 | 4– | 5–10 | 4.0 |
| 123 | 1+ | 2 | 4– | 2–5 | 2.8 |
| 124 | 1+,2– | 3– | 4 | 5–10L | 5.7 |
| 125 | 1+ | 2 | 4–,3+ | 2–5 | 4.3 |
| 126 | 1+ | 2,2+ | 4 | 2–5 | 4.0 |
| 127 | 1+ | 2 | 4– | 2–5 | 3.4 |
| 128 | 1+ | 2 | 4– | 2–5 | 5.1 |
| 129 | 2– | 3+ | 4+ | 5–10 | 7.3 |
| 130 | 1+ | 2– | 4– | 2–5 | 4.1 |
| 131 | 1+ | 2+ | 4+ | 2–5H | 6.2 |
| 131R | 2– | 3,3– | 5,4+ | 5–10 | 6.2 |
| 132 | 1+ | 2,2– | 4 | 2–5 | 3.8 |
| 133 | 1+ | 2,2– | 4,4– | 2–5 | 4.4 |
| 134 | 1+ | 2+ | 4+ | 2–5H | 7.0 |
| 134R | 2– | 3,3= | 5 | 5–10 | 7.0 |
| 135 | 1+ | 1+ | 3+ | 2–5L | 3.1 |
| 136 | 1+ | 2+ | 4– | 2–5H | 4.2 |
| 137 | 1+ | 2,2– | 4– | 2–5 | 4.6 |
| 138 | 1+ | 1+,2– | 4– | 2–5 | 3.6 |
| 139 | 1+ | 1+,2– | 3+ | 2–5 | 4.3 |
| 140 | 1+ | 1+,2– | 4– | 2–5 | 4.4 |
| 141 | 1+ | 2 | 4– | 2–5 | 4.1 |
| 142 | 1+ | 1+ | 3+ | 2–5L | 2.2 |
| 143 | 1+ | 1+ | 3– | 2–5L | 2.0 |
| 144 | 1+ | 2,2– | 4– | 2–5 | 2.6 |
| 145 | 1+ | 1+ | 3+ | 2–5L | 2.7 |
| 146 | 1+ | 1+ | 3 | 2–5L | 2.4 |
| 147 | 1+ | 1+ | 3 | 2–5L | 2.0 |
| 148 | 1+ | 2 | 4– | 2–5 | 2.9 |
| 149 | 2+ | 3+ | 5 | 5–10H | 6.3 |
| 150 | 1+,2– | 3–,2+ | 4+ | 2–5H | 5.3 |
| 151 | 1+ | 1+ | 3+ | 2–5L | 2.4 |
| 152 | 1+ | 1+ | 3+ | 2–5L | 2.6 |
| 153 | 2+ | 3+ | 5 | 5–10H | 9.6 |
| 154 | 1+ | 1+ | 3+ | 2–5L | 4.4 |
| 155 | 1+,2– | 2+ | 4+ | 2–5H | 5.0 |
| 156 | 1+ | 2+ | 4+ | 2–5H | 5.3 |
| 157 | 1+ | 1+,2– | 4– | 2–5 | 3.3 |
| 158 | 1+ | 3 | 5 | 5–10L | 7.8 |
| 159 | 1+ | 1+ | 4– | 2–5L | 3.1 |
| 160 | 1,2– | 3– | 5 | 5–10L | 5.6 |
| 161 | 1+ | 1+ | 3+ | 2–5L | 2.9 |
| 162 | 1+ | 2,2+ | 4 | 2–5 | 5.0 |
| 163 | 2+ | 4– | 5+,6 | 5–10H | 10.7 |
| 164 | 3 | 4 | 5,5+ | >10 | 6.8 |
| 164R | 2+ | 4–,3+ | 5+ | 5–10H | 6.8 |
| 165 | 1+ | 2 | 4 | 2–5 | 3.2 |
| 166 | 1+ | 1+ | 3+ | 2–5L | 2.2 |
| 167 | 1+ | 1+,2– | 4– | 2–5 | 3.2 |
| 168 | 2– | 3– | 5 | 5–10 | 7.4 |
| 169 | 1+ | 2+ | 4+ | 2–5H | 4.4 |
| 170 | 1+,2– | 3 | 5 | 5–10L | 5.7 |
| 171 | 1+ | 2– | 3+ | 2–5 | 3.0 |
| 172 | 1+ | 2– | 3+ | 2–5 | 2.7 |
| 173 | 1+ | 2 | 3+,4– | 2–5 | 2.4 |

TABLE 2-continued

Estimate of Neutrophil Levels

| Sample Number | Color Source 30 sec | 1 min | 2 min | Estimated Neutrophil Range | Count |
|---|---|---|---|---|---|
| 173R | 1+ | 2,2− | 4 | 2−5 | 2.4 |
| 174 | 1+,2− | 2+ | 4+ | 2−5h | 4.2 |
| 175 | 2− | 3 | 4+,5− | 5−10 | 5.6 |
| 176 | 1+ | 1+ | 3 | 2−5L | 2.1 |
| 177 | 2−,1+ | 3− | 4+ | 5−10L | 8.7 |
| 178 | 2+ | 3+,4− | 5+,6 | 5−10H | 7.0 |
| 179 | 1+ | 1+ | 2+,3− | <1 | 2.1 |
| 180 | 1+ | 1+,2− | 4− | 2−5 | 3.3 |
| 181 | 1+,2− | 2 | 4− | 2−5 | 3.9 |
| 182 | 2 | 3,3+ | 5 | 5−10 | 6.6 |
| 183 | 1+,2− | 2+ | 4− | 2−5H | 4.4 |
| 184 | 1+ | 1+,2− | 3+ | 2−5 | 3.3 |
| 185 | 1+ | 2,2+ | 4 | 2−5 | 7.0 |
| 186 | 1+ | 1+,1− | 3+ | 2−5 | 2.8 |
| 187 | 1+ | 2 | 4 | 2−5 | 5.1 |
| 188 | 1+ | 2,2+ | 4 | 2−5 | 5.4 |
| 189 | 1+ | 1+ | 3 | 2−5L | 3.4 |
| 190 | 1+ | 1+,2− | 3+ | 2−5 | 6.9 |
| 190R | 1+ | 2,2− | 3+ | 2−5 | 6.9 |
| 191 | 1+ | 1+,2− | 3+ | 2−5 | 6.3 |
| 191R | 1+ | 1+,2− | 3+ | 2−5 | 6.3 |
| 192 | 1+ | 1+ | 3 | 2−5L | 4.2 |
| 193 | 1+ | 2 | 3+,4 | 2−5 | 6.0 |
| 193R | 1+ | 2+ | 4 | 2−5H | 6.0 |
| 194 | 1+ | 2 | 4− | 2−5 | 5.3 |
| 195 | 1+ | 2 | 4− | 2−5 | 6.5 |
| 195R | 1+ | 2,2+ | 4− | 2−5H | 6.5 |
| 196 | 1+ | 2− | 3,3+ | 2−5 | 4.3 |
| 197 | 1+ | 2+,2− | 3 | 2−5 | 3.0 |
| 198 | 1+ | 1+ | 3 | 2−5L | 3.4 |
| 199 | 1+ | 2 | 4 | 2−5 | 8.9 |
| 199R | 2− | 2,2+ | 4,4− | 2−5 | 8.9 |
| 200 | 1+ | 1+ | 2+ | <2 | 2.6 |

L = low end of range
H = high end of range
R = repeated sample

As will be apparent from the foregoing detailed discussion and examples, the functions of the granulocyte disruption reagent and the indicator are preferably combined in a single assay medium. This medium is preferably formulated as follows:

| Constituent | Concentration |
|---|---|
| Buffer (pH 4.0–7.0) | ca. 50 mM |
| Chromogenic Donor Dye | 0.08 to 2.0 mg/ml |
| 3-Amino-1,2,4-triazole (if an inhibitor is required) | 30 to 75 mM |
| Granulocyte Disruption Reagent | ca. 0.00167%–0.0167% |
| Peroxide | 0.0005 to 0.00065%. |

The invention may be embodied in many forms without departing from the spirit or essential characteristics of the invention. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A method of ascertaining the presence of granulocytes in a sample of whole blood which comprises the steps of:
providing an assay medium which includes a diagnostic system consisting essentially of a peroxide and an oxidation-sensitive indicator which is capable of undergoing a myeloperoxidase-catalyzed color change reaction with said peroxide;
withdrawing the blood sample from a subject;
disrupting red blood cells in the sample by lysis and removing the debris of the disrupted red blood cells by trapping the granulocytes on a membrane and passing said debris through the membrane to isolate said granulocytes and to remove from the blood sample components in the sample that might interfere with a determination of the granulocytes in the sample;
lysing the isolated granulocytes in the blood sample on said membrane to release intracellular myeloperoxidase present in said granulocytes;
bringing the peroxide and indicator in the assay medium into contact with the released myeloperoxidase in that area of the membrane where the myeloperoxidase is released to catalyze color developing reactions between the peroxide and the oxidation-sensitive indicator; and
employing a change in the color of the indicator as evidence of the presence of granulocytes in the blood sample.

2. The method as defined in claim 1 which includes the step of employing the intensity of the color of the indicator after said change of color as a measure of the concentration of granulocytes in the blood sample.

3. The method as defined in claim 1 which includes the step of incorporating in the assay medium an effective amount of an aminothiazole catalase inhibitor.

4. The method as defined in claim 3 in which the catalase inhibitor is 3-amino-1,2,4-triazole.

5. The method as defined in claim 4 in which the concentration of the catalase inhibitor in the assay medium is ca. 30–75 millimolar.

6. The method as defined in claim 1 in which granulocyte cells in the sample are lysed to release myeloperoxidase from said cells by treating said cells with an effective amount of a detergent.

7. The method as defined in claim 6 in which the detergent is hexadecyltrimethylammonium bromide or a polyethylene ether detergent and the concentration of the detergent in the aqueous solution is in the range of 0.00167 to 0.0167 percent.

8. The method as defined in claim 1 in which the peroxide is one of the following: urea hydrogen peroxide, cumene hydroperoxide, hydrogen peroxide or a peroxide formed in vitro by the action of glucose oxidase on glucose.

9. The method as defined in claim 8 in which the peroxide is hydrogen peroxide and said hydrogen peroxide is present in the assay medium in a concentration of ca. 0.0005 to 0.00065 percent.

10. The method as defined in claim 1 in which the oxygen-sensitive indicator is 3,3',5,5'-tetramethylbenzidine.

11. The method as defined in claim 1 which includes the step of including a pH buffer in the assay medium.

12. The method as defined in claim 11 in which the buffer comprises a mixture of phosphates.

13. The method as defined in claim 11 in which the buffer is a citrate buffer with a pH of 4.0 to 5.0.

14. The method as defined in claim 11 in which the buffer comprises a mixture of citrates.

15. The method as defined in claim 11 in which the buffer is a phosphate buffer with a pH of 6.0 to 7.0.

16. The method as defined in claim 1 in which the assay medium includes an organic acid hydrogen donor in an amount effective to delay a change of given magnitude in the color of the oxidation-sensitive indicator.

17. The method as defined in claim 16 in which the proton donor is ascorbic acid in a concentration of not more than one millimole.

18. The method as defined in claim 1 in which the removal of interfering blood components is promoted by applying a pressure to an aqueous medium with which blood sample is lysed.

19. The method as defined in claim 1 in which the level of granulocytes in the blood sample is ascertained by observing the time required for said change in the color of the oxygen-sensitive indicator to occur.

20. The method as defined in claim 1 in which the level of granulocytes in the blood sample is ascertained by determining whether said change in the color of the oxygen-sensitive indicator occurred during a period of selected duration beginning with the time at which the peroxide and the indicator are brought into contact with the released myeloperoxidase.

21. The method as defined in claim 1 in which the granulocyte level of the sample is ascertained by comparing the color of the oxygen-sensitive indicator with a standard having intensities corresponding to different granulocyte counts.

22. The method as defined in claim 1 in which the blood sample is obtained by drawing blood and collecting a sample of the blood with a capillary tube treated so as to inhibit clotting of the blood.

23. The method as defined in claim 22 in which the capillary tube is treated by siliconizing its interior surfaces.

24. The method as defined in claim 22 in which the capillary tube is treated with an anticoagulant.

25. The method as defined in claim 24 in which the anticoagulant is $K_3EDTA$ or sodium heparin.

* * * * *